United States Patent [19]

Paget et al.

[11] 4,338,315

[45] Jul. 6, 1982

[54] ANTIVIRAL METHOD EMPLOYING THIAZINYL BENZIMIDAZOLE DERIVATIVES

[75] Inventors: Charles J. Paget; James W. Chamberlin, both of Indianapolis; James H. Wikel, Greenwood, all of Ind.

[73] Assignee: Eli Lilly and Company, Indianapolis, Ind.

[21] Appl. No.: 265,480

[22] Filed: May 20, 1981

Related U.S. Application Data

[60] Division of Ser. No. 94,129, Nov. 14, 1979, Pat. No. 4,293,558, which is a division of Ser. No. 2,836, Jan. 12, 1979, Pat. No. 4,216,313, which is a division of Ser. No. 769,358, Feb. 16, 1977, Pat. No. 4,150,028, which is a continuation-in-part of Ser. No. 626,014, Oct. 28, 1975, abandoned.

[51] Int. Cl.$^3$ .................. A61K 31/54; A01N 43/86
[52] U.S. Cl. ................................................ 424/246
[58] Field of Search ......................... 424/246; 544/55

[56] References Cited

U.S. PATENT DOCUMENTS 3,825,537  7/1974  Haugwitz et al. ............... 424/246
4,008,243  2/1977  Wikel et al. ...................... 424/246

*Primary Examiner*—Henry R. Jiles
*Assistant Examiner*—Natalia Harkaway
*Attorney, Agent, or Firm*—Charles W. Ashbrook; Arthur R. Whale

[57] ABSTRACT

Certain thiazolinyl or thiazinyl ketobenzimidazole compounds and derivatives thereof are useful as antiviral agents.

36 Claims, No Drawings

ANTIVIRAL METHOD EMPLOYING THIAZINYL BENZIMIDAZOLE DERIVATIVES

CROSS-REFERENCE TO RELATED APPLICATION

This is a division of application Ser. No. 94,129 filed Nov. 14, 1979, now U.S. Pat. No. 4,293,558, which is a division of Ser. No. 2,836 filed Jan. 12, 1979, now U.S. Pat. No. 4,216,313, which is a division of Ser. No. 769,358 filed Feb. 16, 1977, now U.S. Pat. No. 4,150,028, which is a continuation-in-part of Ser. No. 626,014 filed Oct. 28, 1975, now abandoned.

BACKGROUND OF THE INVENTION

The incidence of viral upper respiratory disease is immense. It has been estimated that nearly a billion cases annually appear in the United States alone. Studies performed in England (Tyrell and Bynoe, 1966) indicated that 74 percent of persons having colds were infected with rhinoviruses. Because more than 80 strains of rhinoviruses are already identified, the development of a practical rhinovirus vaccine is not feasible. In this, chemotherapy appears to be the more desirable approach.

The ability of chemical compounds to suppress the growth of viruses in vitro is readily demonstrated by using a virus plaque suppression test similar to that described by Siminoff, *Applied Microbiology*, 9(1), 66(1961).

It is the purpose of this invention to provide a method for suppressing the growth of viruses, particularly rhinoviruses, polio viruses, Coxackie viruses, echo virus, Mengo virus, and influenza. It is a further object to provide novel thiazolinyl or thiazinyl benzimidazole compounds which are useful for suppressing the growth of such viruses.

Certain thiazolinyl or thiazinyl benzimidazole compounds are disclosed in the following references:

U.S. Pat. No. 3,749,717 discloses 1-thiazolinyl- or 1-thiazinyl-2-heterocyclic-benzimidazoles useful as anthelmintic and anti-inflammatory agents.

U.S. Pat. No. 3,825,537 discloses 1-thiazolinyl or 1-thiazinyl-2-aminobenzimidazoles useful as anthelmintic and anti-inflammatory agents.

U.S. Pat. No. 3,833,574 discloses a method of preparing 1-thiazolinyl- or 1-thiazinylbenzimidazolin-2-ones which are anti-inflammatory agents.

Derwent 26199W/16 discloses 1-thiazolinyl- or 1-thiazinyl-2-phenylbenzimidazoles useful as anthelmintic agents.

There is no known prior art reference to antiviral activity of thiazolinyl or thiazinyl benzimidazoles.

SUMMARY OF THE INVENTION

This invention concerns novel thiazolinyl and thiazinyl benzimidazoles, used for suppressing the growth of viruses selected from the group consisting of Coxsackie viruses, echo virus, Mengo virus, polio viruses, rhinoviruses and influenza. The novel benzimidazole compounds are represented by Formula I below:

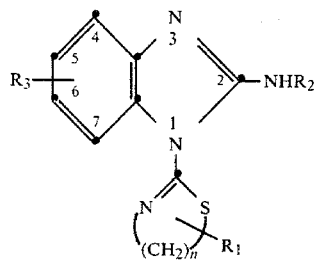

wherein
$R_1$ is hydrogen, $C_1$–$C_3$ alkyl, phenyl, or benzyl;
$R_2$ is hydrogen, or $C_1$–$C_4$ acyl;
$R_3$ is at the 5 or 6 position and is 1-($C_1$–$C_3$ alkyl)-tetrazol-5-yl, 1,3-dithiolan-2-yl,

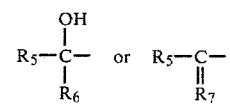

wherein $R_5$ is $C_1$–$C_3$ alkyl, $C_3$–$C_7$ cycloalkyl, ($C_3$–$C_7$ cycloalkyl)methyl, 1-($C_3$–$C_7$ cycloalkyl)ethyl, thienyl, or phenyl; $R_6$ is $C_1$–$C_7$ alkyl; $R_7$ is $C_1$–$C_7$ alkylidene; or

wherein $R_4$ is hydrogen, $C_1$–$C_7$ alkyl, $C_3$–$C_7$ cycloalkyl, ($C_3$–$C_7$ cycloalkyl)methyl, 1-($C_3$–$C_7$ cycloalkyl)ethyl, thienyl, benzyl, phenyl or mono substituted phenyl wherein said substituents are selected from the group consisting of $C_1$–$C_4$ alkyl, $C_1$–$C_4$ alkoxy, chloro, bromo, iodo, nitro or trifluoromethyl and Z is oxygen, hydroxyimino, $C_1$–$C_4$ alkoxyimino, $C_1$–$C_4$ acyloxyimino, hydrazono, α-methoxycarbonylhydrazono, α-hydroxycarbonylmethoxyhydrazono, ethoxycarbonylhydrazono, carbamylhydrazono or thiocarbamylhydrazono; and n is 2 or 3, subject to the limitation that $R_4$ is other than $C_1$–$C_7$ alkyl, benzyl, phenyl, or substituted phenyl when $R_2$ is hydrogen and Z is oxygen.

A preferred group of compounds are those compounds of formula I above wherein
$R_1$ is hydrogen, $C_1$–$C_3$ alkyl, phenyl or benzyl;
$R_2$ is hydrogen or $C_1$–$C_4$ acyl;
$R_3$ is at the 5 or 6 position and is

wherein $R_4$ is hydrogen, $C_1$–$C_7$ alkyl, $C_3$–$C_7$ cycloalkyl, ($C_3$–$C_7$ cycloalkyl)methyl, 1-($C_3$–$C_7$ cycloalkyl)ethyl, benzyl, phenyl or mono substituted phenyl wherein said substituents are selected from the group consisting of $C_1$–$C_4$ alkyl, $C_1$–$C_4$ alkoxy, chloro, bromo, iodo, nitro or trifluoromethyl and Z is oxygen, hydroxyimino, $C_1$–$C_4$ alkoxyimino, $C_1$–$C_4$ acyloxy imino, hydrazono, ethoxycarbonylhydrazono, carbamylhydrazono or thiocarbamylhydrazono; and n is 2 or 3, subject to the limitation that $R_4$ is other than $C_1$-$C_7$ alkyl, benzyl, phenyl or substituted phenyl when $R_2$ is hydrogen and Z is oxygen.

Another preferred group of compounds are those compounds of formula I above wherein $R_1$ is hydrogen; n is 2; $R_2$ is hydrogen; and $R_3$ is

wherein $R_5$ and $R_7$ are defined as before.

DETAILED DESCRIPTION AND PREFERRED EMBODIMENT

The present invention relates to thiazolinyl and thiazinyl benzimidazole compounds, useful in suppressing the growth in mammals of certain viruses including rhinovirus, polio, coxsackie, echo virus, Mengo virus and influenza. The compounds useful in the process of this invention are prepared by reacting the salt (III) of a tautomeric benzimidazole compound represented by the formula II with an aliphatic haloalkylisothiocyanate of the Formula IV, $X-(CH_2)_n-NCS$, which can be optionally substituted on the carbon chain with $R_1$ groups wherein $R_1$, $R_3$, and n are as defined hereinabove and X is chloro or bromo, to yield a compound of Formula V (Formula I above wherein $R_2$ is hydrogen, and $R_3$ is 1-($C_1$-$C_3$ alkyl)-tetrazol-5-yl, 1,3-dithiolan-2-yl, or

wherein Z is oxygen).

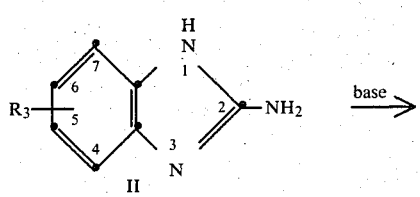

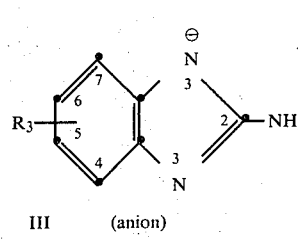

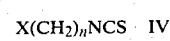

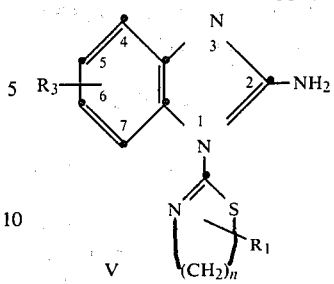

The compounds of formula V above wherein Z is oxygen can be further reacted with a hydroxylamine, hydrazine, ethyl carbazate, carboxymethoxylamine, semicarbazide, $C_1$-$C_4$ alkoxycarbonylamine, α-hydroxycarbonylmethoxyamine, carbamylamine, or thiosemicarbazide to obtain the compounds of formula I wherein Z is hydroxyimino, hydrazono, α-methoxycarbonylhydrazono, α-hydroxycarbonylmethoxyhydrazono, ethoxycarbonylhydrazono, carbamylhydrazono, carboxymethoxylhydrazono, semicarbamylhydrazono, or thiocarbamylhydrazono. The compounds thus formed wherein Z is hydroxyimino can be alkylated to provide the compounds of formula I wherein Z is $C_1$-$C_4$ alkoxyimino or can be acylated to provide the compounds of formula I wherein Z is $C_1$-$C_4$ acyloxyimino and/or $R_2$ is $C_1$-$C_4$ acyl.

The compounds of formula I wherein $R_3$ is

are prepared from the compounds of formula I wherein Z is oxygen by reaction with a $C_1$-$C_7$ alkyl magnesium halide or $C_1$-$C_7$ alkyl lithium followed by hydrolysis. When the compounds of formula I wherein $R_3$ is

are dehydrated the compounds of formula I wherein $R_3$ is

are provided.

The term "tautomeric benzimidazole" refers to a benzimidazole reagent which can be substituted at either nitrogen atom with a hydrogen atom. The benzimidazole reactant, unsubstituted on nitrogen and bearing an $R_3$ substituent group at the 5-position of the benzene moiety has a corresponding tautomeric form with which it is in equilibrium wherein the substituent resides alternatively at the 6-position. The isomer mixture can be indicated by numbering the alternate positions as 5(6). As a consequence of such tautomerism, the reaction of a 5(6)-substituted benzimidazole salt (III) with the haloalkylisothiocyanate (IV) produces isomeric mixtures of 5- or 6-substituted thiazolinyl or thiazinyl benzimidazoles (V), named herein as 5(6)-substituted compounds.

The following definitions refer to the various terms used throughout this disclosure. The term "$C_1$-$C_7$ alkyl" refers to the straight and branched aliphatic radicals of one to seven carbon atoms including methyl, ethyl, propyl, isopropyl, butyl, isobutyl, sec-butyl, tert-butyl, amyl, isoamyl, sec-amyl, sec-isoamyl(1,2-dimethylpropyl), tert-amyl(1,1-dimethylpropyl), hexyl, isohexyl(4-methylpentyl), sec-hexyl(1-methylpentyl), 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl, heptyl, isoheptyl(5-methylhexyl), sec-heptyl(1-methylhexyl), 1-ethylpentyl, 2,2-dimethylpentyl, 3,3-dimethylpentyl, 4,4-dimethylpentyl, 1,2-dimethylpentyl, 1,3-dimethylpentyl, 1,4-dimethylpentyl, 2,4-dimethyl-3-pentyl, 1,2,3-trimethylbutyl, 1,1,2-trimethylbutyl, 1,1,3-trimethylbutyl, and the like. The term $C_1$-$C_7$ alkyl includes within its definition the terms "$C_1$-$C_3$ alkyl", and "$C_1$-$C_4$ alkyl."

The term "$C_3$-$C_7$ cycloalkyl" refers to the saturated alicyclic rings of three to seven carbon atoms such as cyclopropyl, methylcyclopropyl, cyclobutyl, cyclopentyl, cyclohexyl, 1-, 2-, 3- or 4-methylcyclohexyl and cycloheptyl. The term "($C_3$-$C_7$ cycloalkyl)methyl" refers to a methyl radical substituted with saturated alicyclic rings of three to seven carbon atoms as exemplified above in the term "$C_3$-$C_7$ cycloalkyl." The term "1-($C_3$-$C_7$ cycloalkyl)ethyl" refers to ethyl radicals substituted on the carbon atom in the 1 position with saturated alicyclic rings of three to seven carbon atoms as described above.

The terms "$C_1$-$C_4$ alkoxy," or "$C_1$-$C_4$ alkylthio" include the straight and branched alkyl ether or thioether radicals of one to four carbon atoms as exemplified above by $C_1$-$C_4$ alkyl as defined above. The term "$C_1$-$C_4$ alkylamine" likewise refers to an aliphatic amine of one to four carbon atoms as defined above. The term "$C_1$-$C_4$ alkoxyimino" refers to the O-aliphatic hydroxylimino radical derived from hydroxylamine and an alkyl group of one to four carbon atoms as exemplified above. Methoxyamine hydrochloride is available from commercial sources. Other hydroxylamine derivatives are available by (A) alkylation of acetone oxime by $C_1$-$C_4$ alkyl halides followed by acid hydrolysis, (B) alkylation of N-hydroxyphthalimide followed by hydrazinolysis or (C) alkylation of benzohydroxamic acid followed by acid hydrolysis. The term "$C_1$-$C_4$ acyloxyimino" refers to the acyloxyimino radical of one to four carbon atoms including formyloxyimino, acetoxyimino, propionyloxyimino, butyryloximino, isobutyryloximino, and the like. The term "$C_1$-$C_4$ acyl" refers to the acyl radical of one to four carbon atoms such as formyl, acetyl, propionyl, butyryl, 2-methylpropionyl and the like.

The term "$C_1$-$C_7$ alkylidene" refers to straight and branched radicals of one to seven carbon atoms such as methylene, ethylidene, propylidene, isopropylidene, butylidene, isobutylidene, 3-methyl-2-butylidene, 2,4-dimethyl-3-pentylidene, n-hexylidene, and the like.

The term "thienyl" refers to the thiophene radical attached at the 2 or 3 position.

The term "mono-substituted phenyl" indicates substitution on the benzene moiety with a $C_1$-$C_4$ alkyl, a $C_1$-$C_4$ alkoxy, chloro, bromo, iodo, nitro, or a trifluoromethyl group. The term "thiazolinyl" or "thiazolin-2-yl" refers to the $N_1$ moiety of Formula I wherein n is 2 and indicates a 4,5-dihydrothiazole radical attached at the 2-position which may have substituent groups ($R_1$) on the 4- or 5-positions. The term "thiazinyl" or "thiazin-2-yl" refers to the $N_1$ moiety of Formula I wherein n is 3 and indicates a 5,6-dihydro-4H-1,3-thiazine radical attached at the 2-position which may be substituted on the 4-, 5- or 6-positions by $R_1$ groups. Illustrative of the 2-thiazole or 2-thiazine moieties which are included in the scope of this invention are those which can be substituted in the 4-, 5- or 6-positions with methyl, ethyl, propyl, benzyl or phenyl groups. Illustrative of the carbonyl functions,

which are included in the scope of this invention are formyl, cyclopropylcarbonyl, cyclobutylcarbonyl, cyclopentylcarbonyl, cyclohexylcarbonyl, cycloheptylcarbonyl, 2-cyclopropylacetyl, 2-cyclobutylacetyl, 2-cyclopentylacetyl, 2-cyclohexylacetyl, 2-cycloheptylacetyl, 2-cyclopropylpropionyl, 2-cyclobutylpropionyl, 2-cyclopentylpropionyl, 2-cycloheptylpropionyl, 2-phenylacetyl, benzoyl, or benzoyl substituted by $C_1$-$C_4$ alkyl, $C_1$-$C_4$ alkoxy, chloro, bromo, iodo, nitro or trifluoromethyl.

The compounds of Formula V can be prepared by first converting the appropriately substituted benzimidazole reactant (II) into its salt (III) by employing a base such as a metal hydride; e.g., sodium hydride or potassium hydride; a metal amide; e.g., sodium amide; alkali metal alkoxide, e.g., sodium methoxide, potassium ethoxide or sodium butoxide and the like bases. Anion formation can be brought about in a variety of aprotic solvents such as aromatic hydrocarbons; e.g., benzene, toluene or xylene, or ethers such as ethyl ether, glyme or tetrahydrofuran, at a temperature ranging from about 0° C. to about 150° C. for periods of about one hour to twenty-four hours. A slight excess of the base is desirable; thus the molar ratio of the benzimidazole reactant to base can range from about 1:1 to 1:2.

The benzimidazole anion (III) is reacted with an aliphatic haloalkylisothiocyanate (IV) to yield a thiourea intermediate in situ which undergoes intramolecular alkylation on the sulfur atom to form a 1-thiazolinyl- or 1-thiazinylbenzimidazole product represented by Formula V. The molar ratio of the benzimidazole reactant (II) to haloalkylisothiocyanate (IV) can range from 1:1 to 1:1.5 and the reaction time can vary from about one to twenty-four hours at temperatures from about 25° C. to about 150° C. The methods and conditions for preparing the 1-thiazolinyl- or 1-thiazinylbenzimidazole products are analogous to those disclosed in U.S. Pat. Nos. 3,749,717 and 3,825,537.

The thiazolinyl or thiazinyl benzimidazole products are isolated by conventional methods such as filtration and concentration of the filtrate to induce crystallization. Alternatively the reaction mixture can be evaporated to dryness and the residue treated with a suitable solvent such as acetone or methanol to separate and remove any insoluble material. The solution containing the product is concentrated to crystallize the product or is evaporated to give a second residue, which residue is recrystallized from methanol for example. The benzimidazole compound is recovered by filtration or centrifugation.

The reaction of the tautomeric anion (III) with the haloethylisothiocyanate generally provides a 1:1 mixture of 5(6)-isomers of thiazolinyl or thiazinyl benzimidazole product. The 5(6)-isomers are separable by fractional crystallization or by column chromatography. Usually the 6-isomer crystallizes first from a solution of the mixture. Individual isomers except for the 5(6)benzoyl or 5(6)substituted-benzoyl compounds or their derivatives can be unambiguously characterized by their proton magnetic resonance spectra in the phenyl proton region (7.0 to 8.3 ppm).

The thiazolinyl or thiazinyl benzimidazole compounds, wherein $R_2$ is $C_1$–$C_4$ acyl, Z is oxygen and $R_3$ is

can be prepared by reacting the 1-thiazolinyl- or 1-thiazinyl-2-amino-5(6)-substituted-benzimidazoles prepared as above with the anhydrides of acetic, propionic or butyric acid or when $R_2$ is formyl by reaction with the mixed anhydride of formic acid and acetic acid.

The nitrogen derivative of the keto benzimidazole compounds are represented by Formula I above wherein Z is a nitrogen function bonded to the carbon atom of the original carbonyl group ($R_3$ is

where Z is 0). These compounds are prepared by reacting the appropriate 1-thiazolinyl- or 1-thiazinyl-2-substituted-5(6)-keto-benzimidazole with hydroxylamine, $C_1$–$C_4$ alkoxyamine, hydrazine, ethyl carbazate, carboxymethoxylamine, semicarbazide or thiosemicarbazide or their salts in the conventional manner. When the carbonyl (keto) function reacts sluggishly with the carbonyl reagent it can be activated by protonating the keto compound under acidic conditions. Upon protonation subsequent carbon-nitrogen double bond formation occurs readily.

The nitrogen function Z in

is named according to the carbonyl reagent from which it is derived as follows:

| carbonyl reagent | Z (function) | Z (name) |
|---|---|---|
| hydroxylamine | =N—OH | hydroxyimino |
| methoxyamine | =N—OCH$_3$ | methoxyimino |
| ethoxyamine | =N—OC$_2$H$_5$ | ethoxyimino |
| propoxyamine | =N—OC$_3$H$_7$ | propoxyimino |
| butyroxyamine | =N—OC$_4$H$_9$ | butyroxyimino |
| hydrazine | =NNH$_2$ | hydrazono |
| semicarbazide | =NNHC(O)NH$_2$ | carbamylhydrazono |
| thiosemicarbazide | =NNHC(S)NH$_2$ | thiocarbamylhydrazono |
| ethyl carbazate | =NNHCO$_2$C$_2$H$_5$ | ethoxycarbonylhydrazono |
| carboxymethoxylamine | =NOCH$_2$CO$_2$H | hydroxycarbonylmethoxyimino |

The compounds wherein Z is $C_1$–$C_4$ acyloxyimino can be prepared by reacting a compound of Formula I wherein Z is hydroxyimino (=N—OH) with the anhydrides of acetic, propionic or butyric acids. A hydroxyimino compound of the Formula I wherein $R_2$ is hydrogen can be reacted with one equivalent of a $C_1$–$C_4$ acid anhydride to affect O-acylation selectively to provide the products wherein $R_2$ is hydrogen and Z is $C_1$–$C_4$ acyloxyimino. A hydroxyimino compound of Formula I wherein $R_2$ is hydrogen can also be reacted with a molar excess of a $C_1$–$C_4$ acid anhydride to provide the diacylated products wherein $R_2$ is $C_1$–$C_4$ acyl and Z is $C_1$–$C_4$ acyloxyimino and both acyl functions are the same. A hydroxyimino compound of Formula I wherein $R_2$ is $C_1$–$C_4$ acyl can be reacted with one equivalent of a the same or a different $C_1$–$C_4$ acid anhydride to provide the products wherein $R_2$ is $C_1$–$C_4$ acyl and Z is $C_1$–$C_4$ acyloxyimino and the acyl functions may be the same or different. For example, when 1-(thiazolin-2-yl)-2-amino-5(6)-(α-hydroxyiminobenzyl)benzimidazole is reacted at elevated temperatures with one equivalent of acetic anhydride, the mono acylated product, 1-(thiazolin-2-yl)-2-amino-5(6)-(α-acetoxyiminobenzyl)benzimidazole, is obtained. When the same compound is reacted with at least two equivalents of acetic anhydride the diacylated product, 1-(thiazolin-2-yl)-2-acetamido-5(6)-(α-acetoxyiminobenzyl)benzimidazole, is obtained.

When the compounds of formula I are desired wherein $R_3$ is

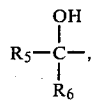

the appropriate 5(6)-ketobenzimidazole is reacted with an appropriate Grignard reagent, e.g. $C_1$–$C_7$ alkyl magnesium halide, or $C_1$–$C_7$ alkyl lithium, and the resulting metal salt or complex is hydrolyzed. The preferred solvents for the alkylation process are inert organic solvents such as tetrahydrofuran; aromatics, such as benzene or toluene; and ethers, such as diethyl ether.

When the compounds of formula I are desired wherein $R_3$ is

the corresponding compound of formula I wherein $R_3$ is

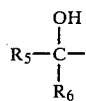

is dehydrated, by procedures known in the art. Suitable dehydration agents are strong acids such as p-toluenesulfonic acid, sulfuric acid, trifluoroacetic acid, methanesulfonic acid, trifluoromethanesulfonic acid, or the like. The preferred solvents for the dehydration process are alkanes, such as hexane and the like; aromatics such as benzene, toluene or the like; chloronated alkanes, such as methylene chloride, chloroform or the like. The temperature range usually employed for the reaction is from about 25° C. to the reflux temperature of the solvent.

The most preferred compounds are those nitrogen derivatives wherein Z is hydroxyimino, $C_1$–$C_4$ acyloxyimino, ethoxycarbonylhydrazono, carbamylhydrazono, or thiocarbamylhydrazono, and the compounds wherein $R_3$ is

$R_1$ is hydrogen, $R_2$ is hydrogen, and n is 2. The 6-isomers of such compounds are preferred over the 5-isomers.

It will be appreciated by those skilled in the art that advantageous chemical operations can be performed at optional stages of product synthesis. For example the benzimidazole reactant can first be chemically modified to provide desired substituents and then reacted with the appropriate haloalkylisothiocyanate to provide the thiazolinyl or thiazinyl benzimidazole product. Alternatively a 1-thiazolinyl- or 1-thiazinylbenzimidazole compound can be prepared initially and then be modified chemically to provide the final desired product. Since the insertion of the thiazolinyl or thiazinyl moiety into the benzimidazole reactant requires reaction with base, those benzimidazole reactants are preferred which have substituent groups which are not susceptible to attack by base. For example, in those compounds wherein $R_2$ is $C_1-C_4$ acyl or Z is a nitrogen function, which compounds have some instability in base, it is preferred that the acyl or nitrogen function be introduced after the thiazoline or thiazine moiety has been formed.

The required keto benzimidazole reactants in which $R_4$ is other than hydrogen can be prepared from the appropriate keto o-phenylenediamine compounds by methods known to the benzimidazole art. For example, Belgian published application No. 93791 discloses the preparation of keto o-phenylenediamines of the formula

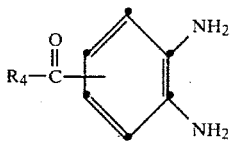

wherein $R_4$ is lower alkyl, cycloalkyl, phenyl or phenyl substituted by halogen, lower alkyl or lower alkoxy. The method of preparation involves the ammonolysis and reduction of a 4-halo-3-nitrophenyl ketone, prepared by the Friedel-Crafts reaction of either (1) a 4-halo-3-nitrobenzoyl chloride with an appropriate hydrocarbon or (2) a halobenzene with an appropriate acid chloride followed by aromatic nitration. Such methods make available the required keto o-phenylenediamines wherein $R_4$ in the formula above is additionally ($C_3-C_7$ cycloalkyl)methyl, 1-($C_3-C_7$ cycloalkyl)ethyl, thienyl or benzyl. Alternatively the keto benzimidazole reactants can be prepared from acetanilide by a Friedel-Crafts acylation with the appropriate derivative of a $C_2-C_8$ alkanoic acid, a $C_3-C_7$ cycloalkyl carboxylic acid, a $C_3-C_7$ cycloalkylacetic acid, a 2-($C_3-C_7$ cycloalkyl)propionic acid, phenyl acetic acid, benzoic acid or benzoic acid substituted by $C_1-C_4$ alkyl, $C_1-C_4$ alkoxy, chloro, bromo, iodo, nitro or trifluoromethyl. The resulting 4-keto acetanilide is nitrated to give a 2-nitro-4-ketoacetanilide and the acetanilide is hydrolyzed to provide a 2-nitro-4-ketoaniline. The nitroaniline is hydrogenated catalytically to yield a 4-keto-o-phenylenediamine which is reacted with cyanogen bromide to provide the appropriate 2-amino-5(6)-ketobenzimidazole.

The required keto benzimidazole reactants in which $R_4$ is hydrogen can be prepared from 4-chloro-3-nitrobenzyl alcohol. The benzyl alcohol is ammoniated to give 4-amino-3-nitrobenzyl alcohol which is hydrogenated catalytically to yield 4-hydroxymethyl-o-phenylenediamine. The phenylenediamine is reacted with cyanogen bromide by the methods known to the benzimidazole art to provide 2-amino-5(6)-hydroxymethylbenzimidazole. The hydroxymethyl group of the benzimidazole compound can be oxidized with Jones reagent (a solution of chromic acid and sulfuric acid in water) to provide the corresponding 5(6)-formyl benzimidazole.

Other required benzimidazole reactants can be prepared by cyclizing o-phenylenediamines substituted with 1-($C_1-C_3$ alkyl)-tetrazol-5-yl or 1,3-dithiolan-2-yl groups. The 2-aminobenzimidazole compounds can be prepared by cyclizing the appropriate o-phenylenediamines with cyanogen bromide as described by Buttle et al., *Biol. Chem. J.* 32, 1101 (1938) and British Pat. No. 551,524. The preparation of a variety of benzimidazoles is well documented in Weissberger's *The Chemistry of Heterocyclic Compounds, Imidazole and Its Derivatives* (Interscience Publisher Co., New York, 1953).

The required haloalkylisothiocyanate reactants, Formula IV above, optionally substituted with $C_1-C_3$ alkyl, benzyl or phenyl groups, are readily prepared from their corresponding haloalkyl amines (VI) and thiophosgene:

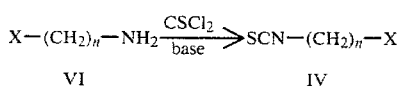

Additional routes for the preparation of haloalkylisothiocyanates (IV) are described in Houben-Weyl's *Methoden Der Orgonischen Chemie*, Vol. 9 (G. Thieme Verlay Stuttgart, 1955). Examples of haloalkylisothiocyanates which can be employed herein include the following:

$SCN(CH_2)_2Br$, $SCN(CH_2)_2Cl$, $SCNCH_2CH(CH_3)Cl$, $SCNCH_2CH(C_6H_5)Br$, $SCN(CH_2)_3Br$, $SCNCH(CH_3)CH_2Cl$, $SCN(CH_2)_3Cl$, $SCNCH_2CH(CH_3)CH_2Br$, $SCNCH(C_2H_5)CH_2Br$, $SCNCH_2CH_2CH(C_6H_5)Br$, $SCNCH_2CH_2CH(C_6H_5)Cl$, $SCNCH(CH_3)CH(CH_3)Cl$, and the like.

The compounds of the invention exhibit a broad spectrum of antiviral activity. Not only are they especially effective in inhibiting the growth of echo virus, Mengo, Coxsackie (A9,21,B5), polio (types I, III, III) or rhinovirus (25 strains) but they also inhibit various types of influenza viruses such as Ann Arbor, Maryland B, Massachusetts B, Hong Kong A, PR-8A and Taylor C (types A,B). The ability of compounds coming within the scope of formula I above to suppress the growth of different viruses in vitro is readily demonstrated by using a plaque suppression test similar to that described by Siminoff, *Applied Microbiology* 9(1), 66–72 (1961). The specific tests utilized are described in detail hereinbelow.

Test Methods

African green monkey kidney cells (BSC-1) or Hela cells (5-3) were grown in 25 cc. Falcon flasks at 37° C. in medium 199 with 5 percent inactivated fetal bovine serum (FBS), penicillin (150 units 1 ml.) and streptomycin (150 mcg./ml.). When confluent monolayers were formed, the supernatant growth medium was removed and 0.3 ml. of an appropriate dilution of virus (echo, Mengo, Coxsackie, polio, or rhinovirus) was added to each flask. After absorption for one hour at room temperature, the virus infected cell sheet was overlaid with a medium comprising one part of 1 percent Ionagar No. 2 and one part double strength medium 199 with FBS, penicillin, and streptomycin which contains drug at concentrations of 100, 50, 25, 12, 6, 3 and 0 micrograms per milliliter (mcg./ml.). The flask containing no drug served as the control for the test. The stock solutions of thiazolinyl or thiazinyl benzimidazole compounds were made up in dimethylsulfoxide at a concentration of $10^4$ mcg./ml. The flasks were incubated for 72 hours at 37° C. for polio, Coxsackie, echo, and Mengo virus and 120 hours at 32° C. for rhinovirus. The influenza viruses, Ann Arbor, Maryland B, Massachusetts B, Hong Kong A, PR-8A, and Taylor C (types A,B), were incubated for 72 hours at 37° C. using MDCK cells (Madin-Darby canine kidney cells). Plaques were seen in those areas where the virus infected and reproduced in the cells. A solution of 10 percent formalin and 2 percent sodium acetate was added to each flask to inactivate the virus and fix the cell sheet to the surface of the flask. The virus plaques, irrespective of size, were counted after staining the surrounding cell areas with crystal violet. The plaque count was compared to the control count at each drug concentration. The activity of the test compound was expressed as percentage plaque reduction, or percent inhibition. Alternatively, the drug concentration, indicated by the symbol $I_{50}$ which inhibits plaque formation by 50 percent can be used as a measure of activity.

Test results are expressed in terms of Polio virus type I inhibition because the virus is easy to grow and consistent test results are obtained. However, the activity of the compounds of this invention was confirmed against other virus cultures such as Coxsackie (A9, A21, B5), echovirus (strains 1-4), Mengo, rhinovirus (25 strains) Polio (type I, II, III), and influenza viruses such as Ann Arbor, Maryland B, Massachusetts B, Hong Kong A, PR-8A and Taylor C (types A,B). Test results for various thiazolinyl or thiazinyl benzimidazole compounds are summarized in Table I below: In the table, column 1 gives the Example number from the chemical examples, column 2 gives the isomer in the 5(6) position, and columns 3-10 indicate the percent virus plaque reduction at drug dilutions from 0.75-100 micrograms per milliliter (mcg/ml).

TABLE I

Polio I Plaque Reduction of 1-(Thiazolin-2-yl)-2-amino-5(6)-substituted-benzimidazoles

| Example No. | Isomer** | Drug Concentration (mcg/ml)* | | | | | | | | |
|---|---|---|---|---|---|---|---|---|---|---|
| | | 100 | 50 | 25 | 12 | 6 | 3 | 1.5 | 0.75 | |
| 9 | 5(6) | 100 | 84 | 67 | 12 | 0 | — | — | — | percent |
| 11 | 5(6) | 100 | 100 | 100 | 98 | 61 | 30 | 21 | 0 | plaque |
| 12 | 5(6) | 100 | 100 | 100 | 100 | 96 | 59 | 22 | 0 | reduction |
| 16 | 5(6) | 100 | 100 | 100 | 100 | 100 | 100 | 96 | 62 | |
| 20 | 5(6) | 41 | 47 | 22 | 0 | 0 | 0 | 0 | 0 | |
| 13 | 5(6) | 58 | 53 | 49 | 39 | 45 | 42 | 0 | 0 | |
| 4 | 5(6) | 100 | 100 | 100 | 100 | 100 | 100 | 78 | 20 | |
| 7 | 5(6) | 100 | 100 | 100 | 100 | 100 | 100 | 100 | 100 | |
| 15 | 5(6) | 100 | 100 | 100 | 100 | 100 | 100 | 100 | 95 | |
| 17 | 5(6) | mod*** tox | sl**** tox | sl tox | 100 | 100 | 100 | 100 | 100 | |
| 19 | 5(6) | 95 | 97 | 87 | 56 | 41 | 16 | 9 | 0 | |
| 14 | 5(6) | 100 | 100 | 100 | 100 | 100 | 100 | 98 | 72 | |
| 28 | 6 | toxic | toxic | sl. toxic | 86 | 43 | 19 | 0 | 0 | |
| 24 | 6 | toxic | toxic | toxic | toxic | 74 | 26 | 7 | 0 | |
| 26 | 6 | toxic | toxic | mod. toxic | 87 | 0 | 0 | 0 | 0 | |
| 27 | 6 | toxic | toxic | mod. toxic | mod. toxic | 100 | 100 | 78 | 22 | |
| 25 | 6 | 33 | 0 | 0 | 0 | 0 | 0 | 0 | 0 | |

*Drug concentration in micrograms per milliliter
**Number 5 or 6 indicates respective isomer; 5(6) indicates isomer mixture.
***mod tox is moderately toxic
****sl tox is slightly toxic The 1-thiazolinyl- or 1-thiazinylbenzimidazole compounds were tested both as pure compounds and as isomer mixtures. Both isomers inhibit virus growth, the 6-isomer generally being more active than the 5-isomer.

Compounds coming within the scope of the above formula are able to suppress the growth of several viruses when added to a medium in which the virus is growing. The compounds of the invention can therefore be used in aqueous solution, preferably with a surfactant, to decontaminate surfaces on which polio, Coxsackie, rhinovirus, and influenza viruses are present, such surfaces including hospital glassware, hospital working surfaces and similar areas used for the preparation of food.

Furthermore, the compounds can be orally administered to warm-blooded animals and humans in a dose of 1 to 300 mg./kg. of animal body weight. The administration can be repeated periodically as needed. In accordance with general practice, the antiviral compound can be administered every four to six hours.

Preferably, the compounds to be employed in accordance with the present invention are used in combination with one or more adjuvants suited to the particular route of administration. Thus, in the case of oral administration, the compound is modified with pharmaceutical diluents or carriers such as lactose, sucrose, starch powder, cellulose, talc, magnesium stearate, magnesium oxide, calcium sulfate, acacia powder, gelatin, sodium alginate, sodium benzoate and stearic acid. Such compositions can be formulated as tablets or enclosed in capsules for convenient administration. In addition, the compounds can be administered parenterally.

The compounds can also be mixed with a liquid and administered as nose drops or intranasal spray.

Preferred compounds useful in the processes of this invention are the 1-(thiazolin-2-yl)-2-amino-5(6)-keto-benzimidazoles wherein the carbonyl function,

$R_4$ is $C_1$–$C_3$ alkyl, phenyl or substituted phenyl.

Illustrative of the preferred thiazolinyl or thiazinyl ketobenzimidazole compounds included in the scope of this invention are the following:

1-(thiazolin-2-yl)-2-propionamido-5(6)-formylbenzimidazole,
1-(thiazin-2-yl)-2-acetamido-5(6)-cyclopropylcarbonylbenzimidazole,
1-(thiazolin-2-yl)-2-(formamido-5(6)-formylbenzimidazole,
1-(thiazin-2-yl)-2-amino-5(6)-(2-cyclopentylacetyl)benzimidazole,
1-(thiazolin-2-yl)-2-propionamide-5(6)-(2-cycloheptylpropionyl)benzimidazole,
1-(4-propylthiazolin-2-yl)-2-acetamido-5(6)-(2-phenylacetyl)benzimidazole,
1-(5-benzylthiazin-2-yl)-2-formamido-5(6)-benzoylbenzimidazole,
1-(5-benzylthiazolin-2-yl)-2-amino-5(6)-cyclobutylcarbonylbenzimidazole,
1-(6-methylthiazin-2-yl)-2-propionamido-5(6)-(2-cycloheptylpropionyl)benzimidazole,
1-(4-phenylthiazolin-2-yl)-2-acetamido-5(6)-(2-cyclobutylacetyl)benzimidazole,
1-(thiazin-2-yl)-2-formamido-5(6)-(4-methoxybenzoyl)benzimidazole,
1-(4-ethylthiazolin-2-yl)-2-amino-5(6)-(2-cyclohexylacetyl)benzimidazole,
1-(4-ethylthiazin-2-yl)-2-propionamido-5(6)-cycloheptylcarbonylbenzimidazole,
1-(thiazolin-2-yl)-2-acetamido-5(6)-(2-cyclopropylpropionyl)benzimidazole,
1-(thiazin-2-yl)-2-formamido-5(6)-(4-trifluoromethylbenzoyl)benzimidazole,
1-(5-methylthiazolin-2-yl)-2-amino-5(6)-cyclobutylcarbonylbenzimidazole,
1-(6-benzylthiazin-2-yl)-2-propionamido-5(6)-(2-cycloheptylacetyl)benzimidazole,
1-(thiazolin-2-yl)-2-acetamido-5(6)-(2-chlorobenzoyl)benzimidazole,
1-(5-methylthiazin-2-yl)-2-formamido-5(6)-(4-propylbenzoyl)benzimidazole,
1-(4-benzylthiazolin-2-yl)-2-amino-5(6)-formylbenzimidazole,
1-(thiazin-2-yl)-7-propionamido-5(6)-(3-ethoxybenzoyl)benzimidazole,
1-(5-propylthiazolin-2-yl)-2-acetamido-5(6)-(2-phenylacetyl)benzimidazole,
1-(thiazin-2-yl)-2-formamido-5(6)-(4-nitrobenzoyl)benzimidazole,
1-(thiazolin-2-yl)-2-amino-5(6)-cycloheptylcarbonylbenzimidazole,
1-(5-phenylthiazin-2-yl)-2-propionamido-5(6)-(2-propoxybenzoyl)benzimidazole,
1-(4-phenylthiazolin-2-yl)-2-acetamido-5(6)-(2-phenylacetyl)benzimidazole,
1-(thiazin-2-yl)-2-formamido-5(6)-cyclobutylcarbonylbenzimidazole,
1-(5-benzylthiazolin-2-yl)-2-amino-5(6)-(2-cyclopentylpropionyl)benzimidazole,
1-(4-propylthiazin-2-yl)-2-propionamido-5(6)-(2-ethylbenzoyl)benzimidazole,
1-(thiazolin-2-yl)-2-acetamido-5(6)-(2-cyclopropylpropionyl)benzimidazole,
1-(thiazin-2-yl)-2-formamido-5(6)-benzoylbenzimidazole,
1-(4-methylthiazolin-2-yl)-2-amino-5(6)-(2-cyclopentylacetyl)benzimidazole,
1-(thiazin-2-yl)-2-propionamido-5(6)-(4-butoxybenzoyl)benzimidazole,
1-(thiazolin-2-yl)-2-acetamido-5(6)-(2-iodobenzoyl)benzimidazole,
1-(4-propylthiazin-2-yl)-2-formamido-5(6)-(2-phenylacetyl)benzimidazole,
1-(5-benzylthiazolin-2-yl)-2-amino-5(6)-(2-cycloheptylpropionyl)benzimidazole,
1-(thiazin-2-yl)-2-propionamido-5(6)-(4-butylbenzoyl)benzimidazole,
1-(thiazolin-2-yl)-2-acetamido-5(6)-formylbenzimidazole,
1-(5-propylthiazin-2-yl)-2-formamido-5(6)-(4-ethoxybenzoyl)benzimidazole,
1-(4-phenylthiazolin-2-yl)-2-amino-5(6)-(2-cyclobutylpropionyl)benzimidazole,
1-(thiazin-2-yl)-2-propionamido-5(6)-(2-methylbenzoyl)benzimidazole,
1-(thiazolin-2-yl)-2-acetamido-5(6)-cyclohexylcarbonylbenzimidazole,
1-(6-propylthiazin-2-yl)-2-formamido-5(6)-(3-propoxybenzoyl)benzimidazole,
1-(5-benzylthiazolin-2-yl)-2-amino-5(6)-(2-cyclobutylpropionyl)benzimidazole,
1-(thiazin-2-yl)-2-propionamido-5(6)-cyclopropylcarbonylbenzimidazole,
1-(thiazolin-2-yl)-2-acetamido-5(6)-(2-nitrobenzoyl)benzimidazole,
1-(6-methylthiazin-2-yl)-2-formamido-5(6)-(2-cyclohexylpropionyl)benzimidazole,
1-(5-methylthiazolin-2-yl)-2-amino-5(6)-(2-cyclopentylacetyl)benzimidazole,
1-(thiazin-2-yl)-2-propionamido-5(6)-(2-bromobenzoyl)benzimidazole,
1-(5-phenylthiazolin-2-yl)-2-amino-5(6)-hydroxyiminomethylbenzimidazole,
1-(4-benzylthiazolin-2-yl)-2-formamido-5(6)-butoxyiminomethylbenzimidazole,
1-(5-propylthiazolin-2-yl)-2-acetamido-5(6)-methoxyiminomethylbenzimidazole,
1-(4-methylthiazolin-2-yl)-2-propionamido-5(6)-hydrazonomethylbenzimidazole,
1-(5-ethylthiazolin-2-yl)-2-amino-5(6)-carbamylhydrazonomethylbenzimidazole,
1-(4-phenylthiazolin-2-yl)-2-propionamido-5(6)-(1-hydroxyiminoethyl)benzimidazole,
1-(5-methylthiazolin-2-yl)-2-acetamido-5(6)-(1-methoxyiminopropyl)benzimidazole,
1-(thiazolin-2-yl)-2-formamido-5(6)-(1-ethoxyiminobutyl)benzimidazole,
1-(4-methylthiazolin-2-yl)-2-amino-5(6)-(1-propoxyiminopentyl)benzimidazole, 1-(5-phenylthiazolin-2-yl)-2-propionamido-5(6)-(1-butoxyiminohexyl)benzimidazole,
1-(4-ethylthiazolin-2-yl)-2-acetamido-5(6)-(1-hydrazonoheptyl)benzimidazole,
1-(5-propylthiazolin-2-yl)-2-amino-5(6)-(1-carbamylhydrazonooctyl)benzimidazole,
1-(thiazolin-2-yl)-2-propionamido-5(6)-(1-thiocarbamylhydrazonoethyl)benzimidazole,
1-(4-propylthiazolin-2-yl)-2-amino-5(6)-(α-hydroxyiminocyclopropylmethyl)benzimidazole,
1-(thiazolin-2-yl)-2-propionamido-5(6)-(α-methoxyiminocyclobutylmethyl)benzimidazole,
1-(5-benzylthiazolin-2-yl)-2-acetamido-5(6)-(α-ethoxyiminocyclopentylmethyl)benzimidazole,
1-(thiazolin-2-yl)-2-formamido-5(6)-(α-propoxyiminocyclohexylmethyl)benzimidazole,
1-(5-propylthiazolin-2-yl)-2-amino-5(6)-(α-butyoxyiminocycloheptylmethyl)benzimidazole,
1-(thiazolin-2-yl)-2-propionamido-5(6)-(α-hydrazonocyclopropylmethyl)benzimidazole,
1-(5-methylthiazolin-2-yl)-2-acetamido-5(6)-(α-carbamylhydrazonocyclobutylmethyl)benzimidazole,
1-(thiazolin-2-yl)-2-formamido-5(6)-(α-thiocarbamylcyclopentylmethyl)benzimidazole,
1-(4-ethylthiazolin-2-yl)-2-amino-5(6)-(1-hydroxyimino-2-cyclopropylethyl)benzimidazole,
1-(thiazolin-2-yl)-2-propionamido-5(6)-(1-methoxyimino-2-cyclobutylethyl)benzimidazole,
1-(thiazin-2-yl)-2-acetamido-5(6)-(1-ethoxyimino-2-cyclopentylethyl)benzimidazole,
1-(6-phenylthiazin-2-yl)-2-formamido-5(6)-(1-propoxyimino-2-cyclohexylethyl)benzimidazole,
1-(4-methylthiazin-2-yl)-2-amino-5(6)-(1-butoxyimino-2-cycloheptylethyl)benzimidazole,
1-(5-propylthiazin-2-yl)-2-propionamido-5(6)-(1-hydrazono-2-cyclopropylethyl)benzimidazole,
1-(4-benzylthiazin-2-yl)-2-acetamido-5(6)-(1-carbamylhydrazono-2-cyclobutylethyl)benzimidazole,
1-(thiazolin-2-yl)-2-formamido-5(6)-(1-thiocarbamylhydrazono-2-cyclopentylethyl)benzimidazole,
1-(5-propylthiazin-2-yl)-2-amino-5(6)-(1-hydroxyimino-2-cyclopropylpropyl)benzimidazole,
1-(4-ethylthiazin-2-yl)-2-propionamido-5(6)-(1-methoxyimino-2-cyclobutylpropyl)benzimidazole,
1-(thiazin-2-yl)-2-acetamido-5(6)-(1-ethoxyimino-2-cyclopentylpropyl)benzimidazole,
1-(6-methylthiazin-2-yl)-2-formamido-5(6)-(1-propoxyimino-2-cyclohexylpropyl)benzimidazole,
1-(4-ethylthiazin-2-yl)-2-amino-5(6)-(1-butoxyimino-2-cycloheptylpropyl)benzimidazole,
1-(thiazolin-2-yl)-2-propionamido-5(6)-(1-hydrazono-2-cyclopropylpropyl)benzimidazole,
1-(5-propylthiazin-2-yl)-2-acetamido-5(6)-(1-carbamylhydrazono-2-cyclobutylpropyl)benzimidazole,
1-(4-propylthiazolin-2-yl)-2-formamido-5(6)-(1-thiocarbamylhydrazono-2-cyclopentylpropyl)benzimidazole,
1-(thiazolin-2-yl)-2-amino-5(6)-(α-hydroxyiminobenzyl)benzimidazole,
1-(thiazin-2-yl)-2-propionamido-5(6)-(α-methoxyiminobenzyl)benzimidazole,
1-(5-ethylthiazolin-2-yl)-2-acetamido-5(6)-(α-ethoxyiminobenzyl)benzimidazole,
1-(5-benzylthiazin-2-yl)-2-formamido-5(6)-(α-propoxyiminobenzyl)benzimidazole,
1-(thiazolin-2-yl)-2-amino-5(6)-(α-butoxyiminobenzyl)benzimidazole,
1-(4-phenylthiazin-2-yl)-2-propionamido-5(6)-(α-hydrazonobenzyl)benzimidazole,
1-(5-methylthiazolin-2-yl)-2-acetamido-5(6)-(α-carbamylhydrazonobenzyl)benzimidazole,
1-(4-propylthiazin-2-yl)-2-formamido-5(6)-(α-thiocarbamylhydrazonobenzyl)benzimidazole,
1-(5-ethylthiazolin-2-yl)-2-propionamido-5(6)-(α-hydroxyimino-2-methylbenzyl)benzimidazole,
1-(thiazin-2-yl)-2-acetamido-5(6)-(α-methoxyimino-3-ethylbenzyl)benzimidazole,
1-(4-benzylthiazolin-2-yl)-2-formamido-5(6)-(α-ethoxyimino-4-propylbenzyl)benzimidazole,
1-(4-methylthiazin-2-yl)-2-amino-5(6)-(α-propoxyimino-2-butylbenzyl)benzimidazole,
1-(thiazolin-2-yl)-2-propionamido-5(6)-(α-butoxyimino-3-methylbenzyl)benzimidazole,
1-(5-phenylthiazin-2-yl)-2-acetamido-5(6)-(α-hydrazono-2-methoxybenzyl)benzimidazole,
1-(4-propylthiazolin-2-yl)-2-formamido-5(6)-(α-carbamylhydrazono-3-chlorobenzyl)benzimidazole,
1-(thiazin-2-yl)-2-amino-5(6)-(α-thiocarbamylhydrazono-2-iodobenzyl)benzimidazole,
1-(thiazolin-2-yl)-2-propionamido-5(6)-(α-hydrazono-4-trifluoromethylbenzyl)benzimidazole,
1-(6-methylthiazin-2-yl)-2-acetamido-5(6)-(α-ethoxyimino-4-chlorobenzyl)benzimidazole,
1-(5-benzylthiazolin-2-yl)-2-formamido-5(6)-(α-hydrazono-4-propoxybenzyl)benzimidazole,
1-(5-methylthiazin-2-yl)-2-amino-5(6)-(α-thiocarbamylhydrazono-4-nitrobenzyl)benzimidazole,
1-(4-ethylthiazolin-2-yl)-2-propionamido-5(6-(α-propoxyimino-2-methoxybenzyl)benzimidazole,
1-(thiazin-2-yl)-2-acetamido-5(6)-(α-hydrazono-2-trifluoromethylbenzyl)benzimidazole,
1-(thiazin-2-yl)-2-amino-5(6)-(α-ethoxycarbonylhydrazono-2-iodobenzyl)benzimidazole,
1-(thiazolin-2-yl)-2-butyramido-5(6)-(α-ethoxycarbonylhydrazono-4-trifluoromethylbenzyl)benzimidazole,
1-(thiazolin-2-yl)-2-amino-5(6)-(α-ethoxycarbonylhydrazono-4-propoxybenzyl)benzimidazole,
1-(thiazolin-2-yl)-2-butyramido-5(6)-(1-ethoxycarbonylhydrazono-2-cyclohexylpropyl)benzimidazole,
1-(thiazolin-2-yl)-2-amino-5(6)-(1-ethoxycarbonylhydrazono-2-cyclobutylpropyl)benzimidazole,
1-(thiazolin-2-yl)-2-butyramido-5(6)-(α-ethoxycarbonylhydrazonobenzyl)benzimidazole,
1-(4-ethylthiazolin-2-yl)-2-amino-5(6)-(1-ethoxycarbonylhydrazono-2-cyclopropylethyl)benzimidazole,
1-(thiazolin-2-yl)-2-amino-5(6)-(1-ethoxycarbonylhydrazono-2-cycloheptylethyl)benzimidazole,
1-(thiazolin-2-yl)-2-formamido-5(6)-(1-ethoxycarbonylhydrazonobutyl)benzimidazole,
1-(5-methylthiazolin-2-yl)-2-amino-5(6)-(α-ethoxycarbonylhydrazonocyclobutylmethyl)benzimidazole,
1-(thiazolin-2-yl)-2-formamido-5(6)-(α-ethoxycarbonylhydrazonocyclopentylmethyl)benzimidazole,
1-(5-propylthiazin-2-yl)-2-butyramido-5(6)-(1-ethoxycarbonylhydrazono-2-cyclopropylethyl)benzimidazole,
1-(4-benzylthiazin-2-yl)-2-acetamido-5(6)-(1-ethoxycarbonylhydrazono-2-cyclobutylethyl)benzimidazole,
1-(thiazolin-2-yl)-2-amino-5(6)-(1-ethoxycarbonylhydrazono-2-cyclopentylethyl)benzimidazole,
1-(thiazolin-2-yl)-2-butyramido-5(6)-(1-ethoxycarbonylhydrazono-2-cyclopropylpropyl)benzimidazole,
1-(5-propylthiazin-2-yl)-2-amino-5(6)-(1-ethoxycarbonylhydrazono-2-cyclobutylpropyl)benzimidazole, 1-(thiazolin-2-yl)-2-butyramido-5(6)-(α-ethoxycarbonylhydrazonocyclopropylmethyl)benzimidazole,
1-(6-phenylthiazin-2-yl)-2-butyramido-5(6)-(1-acetoxyimino-2-cyclohexylethyl)benzimidazole,
1-(4-methylthiazin-2-yl)-2-amino-5(6)-(1-propionyloxyimino-2-cycloheptylethyl)benzimidazole,
1-(5-propylthiazin-2-yl)-2-butyramido-5(6)-(1-butyryloxyimino-2-cyclopropylethyl)benzimidazole,
1-(5-propylthiazin-2-yl)-2-amino-5(6)-(1-formyloxyimino-2-cyclopropylpropyl)benzimidazole,
1-(4-ethylthiazin-2-yl)-2-butyramido-5(6)-(1-acetoxyimino-2-cyclobutylpropyl)benzimidazole,
1-(thiazin-2-yl)-2-acetamido-5(6)-(1-propionyloxyimino-2-cyclopentylpropyl)benzimidazole,
1-(6-methylthiazin-2-yl)-2-butyramido-5(6)-(1-butyryloxyimino-2-cyclohexylpropyl)benzimidazole,
1-(4-ethylthiazin-2-yl)-2-amino-5(6)-(1-formyloxyimino-2-cycloheptylpropyl)benzimidazole,
1-(thiazolin-2-yl)-2-amino-5(6)-(α-acetoxyiminobenzyl)benzimidazole,
1-(thiazin-2-yl)-2-butyramido-5(6)-(α-propionyloxyiminobenzyl)benzimidazole,
1-(5-ethylthiazolin-2-yl)-2-acetamido-5(6)-(α-butyryloxyiminobenzyl)benzimidazole,
1-(5-benzylthiazin-2-yl)-2-butyramido-5(6)-(α-formyloxyiminobenzyl)benzimidazole,
1-(thiazolin-2-yl)-2-amino-5(6)-(α-acetoxyiminobenzyl)benzimidazole,
1-(5-phenylthiazolin-2-yl)-2-amino-5(6)-acetoxyiminomethylbenzimidazole,
1-(4-benzylthiazolin-2-yl)-2-formamido-5(6-propionyloxyiminomethylbenzimidazole,
1-(5-propylthiazolin-2-yl)-2-acetamido-5(6)-formyloxyiminomethylbenzimidazole,
1-(4-phenylthiazin-2-yl)-2-propionamido-5(6)-(1-butyryloxyiminoethyl)benzimidazole,
1-(5-methylthiazolin-2-yl)-2-acetamido-5(6)-(1-formyloxyiminopropyl)benzimidazole,
1-(thiazolin-2-yl)-2-formamido-5(6)-(1-acetoxyiminobutyl)benzimidazole,
1-(4-methylthiazolin-2-yl)-2-amino-5(6)-(1-propionyloxyiminopentyl)benzimidazole,
1-(5-phenylthiazolin-2-yl)-2-propionamido-5(6)-(1-butyryloxyiminohexyl)benzimidazole,
1-(4-propylthiazolin-2-yl)-2-amino-5(6)-(α-formyloxyiminocyclopropylmethyl)benzimidazole,
1-(thiazolin-2-yl)-2-propionamido-5(6)-(α-acetoxyiminocyclobutylmethyl)benzimidazole,
1-(5-benzylthiazolin-2-yl)-2-acetamido-5(6)-(α-propionyloxyiminocyclopentylmethyl)benzimidazole,
1-(thiazolin-2-yl)-2-formamido-5(6)-(α-butyryloxyiminocyclohexylmethyl)benzimidazole,
1-(5-propylthiazolin-2-yl)-2-amino-5(6)-(α-formyloxyiminocycloheptylmethyl)benzimidazole,
1-(thiazolin-2-yl)-2-propionamido-5(6)-(α-acetoxyiminocyclopropylmethyl)benzimidazole,
1-(4-ethylthiazolin-2-yl)-2-butyramido-5(6)-(1-propionyloxyimino-2-cyclopropylethyl)benzimidazole,
1-(5-phenylthiazin-2-yl)-2-butyramido-5(6)-(α-ethoxycarbonylhydrazono-2-methoxybenzyl)benzimidazole,
1-(4-propylthiazolin-2-yl)-2-formamido-5(6)-(α-ethoxycarbonylhydrazono-3-chlorobenzyl)benzimidazole,
1-(5-ethylthiazolin-2-yl)-2-butyramido-5(6)-(α-propionyloxyimino-2-methylbenzyl)benzimidazole,
1-(thiazin-2-yl)-2-acetamido-5(6)-(α-butyryloxyimino-3-ethylbenzyl)benzimidazole,
1-(4-benzylthiazolin-2-yl)-2-butyramido-5(6)-(α-formyloxyimino-4-propylbenzyl)benzimidazole,
1-(4-methylthiazin-2-yl)-2-amino-5(6)-(α-acetoxyimino-2-butylbenzyl)benzimidazole,
1-(thiazolin-2-yl)-2-butyramido-5(6)-(α-propionyloxyimino-3-methylbenzyl)benzimidazole,
1-(6-methylthiazin-2-yl)-2-acetamido-5(6)-(α-butyryloxyimino-4-chlorobenzyl)benzimidazole,
1-(4-ethylthiazolin-2-yl)-2-butyramido-5(6)-(α-formyloxyimino-2-methoxybenzyl)benzimidazole,
1-(5-benzylthiazin-2-yl)-2-acetamido-5(6)-(α-acetoxyiminocyclopentylmethyl)benzimidazole,
1-(thiazolin-2-yl)-2-formamido-5(6)-(α-propionyloxyiminocyclohexylmethyl)benzimidazole,
1-(5-propylthiazolin-2-yl)-2-butyramido-5(6)-(α-butyryloxyiminocycloheptylmethyl)benzimidazole,
1-(4-ethylthiazolin-2-yl)-2-amino-5(6)-(1-formyloxyimino-2-cyclopropylethyl)benzimidazole,
1-(thiazolin-2-yl)-2-butyramido-5(6)-(1-acetoxyimino-2-cyclobutylethyl)benzimidazole,
1-(thiazin-2-yl)-2-acetamido-5(6)-(1-propionyloxyimino-2-cyclopentylethyl)benzimidazole,
1-(4-propylthiazolin-2-yl)-2-acetamido-5(6)-(1-ethoxycarbonylhydrazono-2-cyclopentylpropyl)benzimidazole,
1-(4-phenylthiazin-2-yl)-2-butyramido-5(6)-(α-ethoxycarbonylhydrazonobenzyl)benzimidazole,
1-(5-methylthiazolin-2-yl)-2-amino-5(6)-(α-ethoxycarbonylhydrazonobenzyl)benzimidazole,
1-(4-propylthiazin-2-yl)-2-formamido-5(6)-(α-ethoxycarbonylhydrazonobenzyl)benzimidazole,
1-(4-ethylthiazolin-2-yl)-2-butyramido-5(6)-(1-ethoxycarbonylhydrazonoheptyl)benzimidazole,
1-(thiazolin-2-yl)-2-formamido-5(6)-(α-ethoxycarbonylhydrazonocyclopropylmethyl)benzimidazole,
1-(5-propylthiazin-2-yl)-2-amino-5(6)-(1-ethoxycarbonylhydrazono-2-cyclopropylethyl)benzimidazole,
1-(thiazolin-2-yl)-2-butyramido-5(6)-(1-ethoxycarbonylhydrazono-2-cyclopropylpropyl)benzimidazole,
1-(4-phenylthiazin-2-yl)-2-propionamido-5(6)-(α-ethoxycarbonylhydrazonobenzyl)benzimidazole.
1-(5-phenylthiazin-2-yl)-2-acetamido-5(6)-(α-ethoxycarbonylhydrazono-2-methoxybenzyl)benzimidazole,
1-(thiazolin-2-yl)-2-butyramido-5(6)-(α-ethoxycarbonylhydrazono-4-trifluoromethylbenzyl)benzimidazole,
1-(5-benzylthiazolin-2-yl)-2-formamido-5(6)-(α-ethoxycarbonylhydrazono-4-propylbenzyl)benzimidazole,
1-(thiazin-2-yl)-2-acetamido-5(6)-(α-ethoxycarbonylhydrazono-2-trifluoromethylbenzyl)benzimidazole,
1-(5-ethylthiazolin-2-yl)-2-amino-5(6)-(ethoxycarbonylhydrazonomethyl)benzimidazole,
1-(5-propylthiazolin-2-yl)-2-butyramido-5(6)-(1-ethoxycarbonylhydrazonooctyl)benzimidazole,
1-(thiazolin-2-yl)-2-acetamido-5(6)-(1-ethoxycarbonylhydrazonoethyl)benzimidazole,
1-(thiazolin-2-yl)-2-butyramido-5(6)-(α-ethoxycarbonylhydrazonocyclopropylmethyl)benzimidazole,
1-(6-phenylthiazin-2-yl)-2-butyramido-5(6)-(1-butyryloxyimino-2-cyclohexylethyl)benzimidazole,
1-(thiazolin-2-yl)-2-butyramido-5(6)-(1-butyryloxyimino-2-cyclobutylethyl)benzimidazole,
1-(thiazin-2-yl)-2-butyramido-5(6)-(1-formyloxyimino-2-cyclopentylethyl)benzimidazole,
1-(5-propylthiazolin-2-yl)-2-formamido-5(6)-(α-carbamyhydrazono-4-propylbenzyl)benzimidazole, and 1-(4-phenylthiazin-2-yl)-2-amino-5(6)-(α-thiocarbamyl-2-methoxybenzyl)benzimidazole.

Illustrative of the preferred thiazolinyl benzimidazole compounds included in the scope of formula (I) are the following:

1-(thiazolin-2-yl)-2-amino-5(6)-(α-hydroxy-α-methylbenzyl)benzimidazole, 1-(thiazolin-2-yl)-2-amino-5(6)-(α-methylenebenzyl)benzimidazole, 1-(thiazolin-2-yl)-2-amino-5(6)-(α-ethylidenebenzyl)benzimidazole, 1-(thiazolin-2-yl)-2-amino-5(6)-(α-hydroxy-α-n-hexylbenzyl)benzimidazole, 1-(thiazolin-2-yl)-2-amino-5(6)-(α-n-hexylidenebenzyl)benzimidazole, 1-thiazolin-2-yl)-2-amino-5(6)-[α-hydroxy-α-(2,4-dimethyl-3-pentyl)benzyl]benzimidazole, 1-(thiazolin-2-yl)-2-amino-5(6)-[α-(2,4-dimethyl-3-pentylidene)benzyl]benzimidazole, The following examples illustrate further the preparation of starting materials, intermediates, and compounds of the invention.

EXAMPLES 1–4

1-(thiazolin-2-yl)-2-amino-5(6)-substituted-benzimidazoles (general procedure)

Five millimoles, 140 mg., of sodium hydride as a 50 percent suspension in mineral oil is washed with n-pentane about three times by decanting off the washings. The washed sodium hydride is suspended in 5 ml. of dimethylformamide under anhydrous conditions. Five millimoles of the appropriate 2-amino-5(6)-substituted-benzimidazole dissolved in 25 ml. of dimethoxyethane (glyme) or a mixture of glyme and dimethylformamide (DMF) (15:1 ratio) is added dropwise with stirring to the base suspension. Stirring is continued for several hours at room temperature to allow substantially complete anion formation. Five millimoles, 605 mg., of chloroethylisothiocyanate in DMF is added dropwise to the anion solution and stirring is continued overnight. The reaction mixture is evaporated to dryness in vacuo. The residue is taken up in ethyl acetate and filtered. The ethyl acetate filtrate is washed with water and dried. The 1-(thiazolin-2-yl)-2-amino-5(6)-substituted-benzimidazole product is recovered by evaporation or concentration of the solvent. The product is purified by recrystallization from suitable solvents such as ethyl acetate, chloroform, methanol or mixtures thereof.

The following compounds were prepared by the methods described above from the appropriate 2-aminobenzimidazole substituted in the 5(6)-position with the appropriate chloro, nitro, trifluoromethyl, formyl or benzoyl group.

1-(Thiazolin-2-yl)-2-amino-5(6)-chlorobenzimidazole. The yield was 500 mg. (39.7 percent) from 0.005 mole of 2-amino-5(6)-chlorobenzimidazole.

Analysis $C_{10}H_9ClN_4S$ MW 252: Calcd: C, 47.53; H, 3.59; N, 22.17; CL, 14.03. Found: C, 47.48; H, 3.72; N, 21.78; Cl, 14.20.

1-(Thiazolin-2-yl)-2-amino-5(6)-nitrobenzimidazole. The yield was 6 g. (67 percent) from 0.035 mole of 2-amino-5(6)-nitrobenzimidazole.

Analysis $C_{10}H_9N_5O_2S$ MW 263: Calcd: C, 45.62; H, 3.45; N, 26.60. Found: C, 45.60; H, 3.62; N, 26.48.

1-(Thiazolin-2-yl)-2-amino-5(6)-(trifluoromethyl)benzimidazole. The yield was 900 mg. (37 percent) from 0.005 mole of 2-amino-5(6)-trifluoromethylbenzimidazole.

Analysis $C_{11}H_9F_3N_4S$ MW 286: Calcd: C, 46.15; H, 3.17; N, 19.57; F, 19.91. Found: C, 46.47; H, 3.24; N, 19.44; F, 19.50.

1-(Thiazolin-2-yl)-2-amino-5(6)-benzoylbenzimidazole. The yield was 680 mg. (8.3 percent) from 6.4 g. (27 mm) of 2-amino-5(6)-benzoylbenzimidazole.

Analysis $C_{17}H_{15}N_4OS$ MW 323: Calcd: C, 63.34; H, 4.38; N, 17.38; S, 9.93. Found: C, 63.14; H, 4.19; N, 17.08; S, 9.72.

EXAMPLE 5

1-(Thiazolin-2-yl)-2-amino-5(6)-benzoylbenzimidazole

Three-hundred grams (1.52 mole) of 4-aminobenzophenone were added in portions to a stirred solution of 250 ml. of acetic anhydride in 250 ml. of benzene. The temperature of the mixture rose to about 70° C. The reaction mixture was stirred overnight. The precipitated product was filtered, washed with benzene and dried. The yield of 4-acetamidobenzophenone was 333.8 g. (91.5 percent yield), mp. 150°–152° C. (Lit. mp. 155° C., Chem Abst. 55, 18651).

Twenty-three grams (0.1 m.) of 4-acetamidobenzophenone, 50 ml. of acetic anhydride and 20 ml. of acetic acid were stirred together. A solution of 90 percent nitric acid (15 ml.), 10 ml. of acetic acid and 0.2 g. of urea was added dropwise to the benzophenone mixture. The reaction mixture was maintained at a temperature of about 50° C. during the nitration. The mixture was stirred at ambient temperature whereupon the mixture became very thick. The thick slurry was poured over ice and the insoluble product was filtered to yield 17.7 g. (62.5 percent yield) of 4-acetamido-3-nitrobenzophenone.

Analysis $C_{15}N_2O_4$ MW 284.27: Calcd: C, 63.38; H, 4.26; N, 9.85; O, 22.51. Found: C, 63.57; H, 4.03; N, 9.90; O, 22.27.

Ten grams of 4-acetamido-3-nitrobenzophenone was added protion-wise to 40 ml. of sulfuric acid. The reaction temperature was moderated with a water bath. After stirring about 45 minutes the reaction mixture was carefully poured over ice. The precipitated product was filtered to yield 4-amino-3-nitrobenzophenone.

Analysis $C_{13}H_{10}N_2O_3$ MW 243.23: Calcd: C, 64.16; H, 4.16; N, 11.56; O, 19.81. Found: C, 64.19; H, 4.00; N, 11.37; O, 19.72.

Fifty grams of 4-amino-3-nitrobenzophenone was hydrogenated at room temperature in 945 ml. of tetrahydrofuran with 15 g. of Raney nickel at 40 psi. After 4 hours three equivalents of hydrogen were absorbed. The catalyst was filtered and the filtrate was evaporated in vacuo to a solid residue. The residue was chromatographed over silica gel using ethyl acetate as eluant. Fractions 5–9 were combined to yield 43.6 g. (100 percent yield) of 3,4-diaminobenzophenone.

Two-tenths mole, 42.4 g., of 3,4-diaminobenzophenone were dissolved in 100 ml. of methanol and mixed into one liter of water. Two-tenths mole, 21.8 g, of cyanogen bromide were added in portions to the reaction mixture with stirring. The reaction was continued overnight. The reaction mixture was filtered and the filtrate was neutralized (pH=7.00) with concentrated ammonium hydroxide. The precipitated product was collected, washed with water, and dried in a vacuum oven to yield 31 g. (68.5 percent) of 2-amino-5(6)-benzoylbenzimidazole.

Analysis $C_{14}H_{11}N_3O$ MW 237.2: Calcd: C, 70.87; H, 4.67; N, 17.71. Found: C, 70.88; H, 4.60; N, 17.48.

The 2-amino-5(6)-benzoylbenzimidazole was then reacted by the procedure of Example 1 to yield 1-(thiazolin-2-yl)-2-amino-5(6)-benzoylbenzimidazole, identical to the product of Example 4.

EXAMPLE 6

1-(Thiazolin-2-yl)-2-amino-5(6)-aminobenzimidazole.

Three grams (11 mmole) of 1-(thiazolin-2-yl)-2-amino-5(6)-nitrobenzimidazole were hydrogenated with 5 percent palladium-on-carbon in 145 ml. of ethanol at room temperature. After 2 hours hydrogenation was virtually complete and the catalyst was filtered. The ethanol filtrate was evaporated in vacuo to a residue. The product residue was taken up in ethanol-methanol to yield 1.0 g. (39 percent) of 1-(thiazolin-2-yl)-2-amino-5(6)-aminobenzimidazole.

Analysis $C_{10}H_{11}N_5S$ MW 233: Calcd: C, 51.48; H, 4.75; N, 30.02. Found: C, 51.53; H, 5.03; N, 29.84.

EXAMPLE 7

1-(Thiazolin-2-yl)-2-amino-5(6)-($\alpha$-hydroxyiminobenzyl)benzimidazole

Five millimoles, 1.61 g., of 1-(thiazol-2-yl)-2-amino-5(6)-benzoylbenzimidazole, 1.0 g. of hydroxylamine hydrochloride, and 200 ml. of methanol were heated at reflux for about 12 hours. The reaction mixture was concentrated to about one-half the original volume by evaporation on the steam bath. The mixture was diluted with one hundred milliliters of buffer solution (pH=7.00). The precipitated product was collected to yield 650 mg. (40 percent) of 1-(thiazolin-2-yl)-2-amino-5(6)-($\alpha$-hydroxyiminobenzyl)benzimidazole.

Analysis $C_{16}H_{15}N_5OS$ MW 325: Calcd: C, 60.52; H, 4.48; N, 20.76. Found: C, 60.13; H, 4.40; N, 20.37.

EXAMPLE 8

1-(Thiazolin-2-yl)-2-amino-5(6)-($\alpha$-thiocarbamylhydrazonobenzyl)benzimidazole One and three tenths grams of 1-(thiazolin-2-yl)-2-amino-5(6)-benzoylbenzimidazole were dissolved in 160 ml. of methanol and 4 ml. of 1 N HCl. Eight hundred milligrams of thiosemicarbazide were added and the mixture was heated at reflux with stirring overnight. The reaction was concentrated to one half the original volume in vacuo. Eighty milliliters of buffer solution (pH=7.00) were added to the mixture. Upon standing the product precipitated. The product was collected to yield 1.3 g. of 1-(thiazolin-2-yl)-2-amino-5(6)-($\alpha$-thiocarbamylhydrazonobenzyl)benzimidazole.

EXAMPLE 9

1-(Thiazolin-2-yl)-2-amino-5(6)-formylbenzimidazole (A) 4-Amino-3-nitrobenzyl alcohol Fifty grams (0.27 mole) of 4-chloro-3-nitrobenzyl alcohol, 250 ml. of methanol and 200 ml. of liquid ammonia were loaded into a cold autoclave. The autoclave was sealed and heated to a temperature of 150° C. After cooling, the autoclave was vented and the volatile constituents removed by evaporation in vacuo. The residue was taken up in ether and the ether solution was filtered to remove ammonium chloride which had precipitated. The ether filtrate was evaporated in vacuo to yield a solid product. The product was recrystallized from 95% ethanol/ethyl acetate to give 23.6 g. (52 percent yield) of 4-amino-3-nitrobenzyl alcohol, mp 100°–101° C.

Analysis: $C_7H_8N_2O_3$ MW 168: Calcd: C, 50.00; H, 4.80; N, 16.66. Found: C, 49.72; H, 4.56; N, 16.44.

(B) 3,4-Diaminobenzyl alcohol

Six grams (0.035 mole) of 4-amino-3-nitrobenzyl alcohol, 95 ml. of tetrahydrofuran and 0.5 g. of Raney Nickel were hydrogenated at 40 psi at room temperature until 3 moles of hydrogen were absorbed. The catalyst was filtered and the filtrate was evaporated in vacuo to yield 4.83 g. (82 percent yield) of 3,4-diaminobenzyl alcohol, mp 74°–75° C.

Analysis: $C_7H_{10}N_2O$ MW 138: Calcd: C, 60.85; H, 7.30; N, 20.28. Found: C, 60.90; H, 7.15; N, 19.99.

(C) 2-Amino-5(6)-hydroxymethylbenzimidazole.

Two grams (0.014 mole) of 3,4-diaminobenzyl alcohol were dissolved in 40 ml. of methanol. To this solution was added a solution of 1.6 g. (0.014 mole) of cyanogen bromide in 10 ml. of methanol. After standing overnight at room temperature, the reaction mixture was evaporated to dryness in vacuo to give 3.4 g. (97 percent yield) of the hydrobromide salt of 2-amino-5(6)-hydroxymethylbenzimidazole.

Alternatively, this product may also be obtained from 4-amino-3-nitrobenzyl alcohol without isolation of the intermediate diamine after hydrogenation. The filtrate obtained after removal of the hydrogenation catalyst was treated with a solution of cyanogen bromide in methanol. The product was isolated as described above.

(D) 2-Amino-5(6)-formylbenzimidazole.

Two hundred and fifty milligrams of 2-amino-5(6)-hydroxymethylbenzimidazole were suspended in 7 ml. of acetone and the mixture was cooled in an ice bath. Jones reagent (0.3 ml) was added to the cold reaction mixture and the reaction was continued at 0° C. for about 5 minutes. The mixture was poured into 40 ml. of water. The aqueous mixture was extracted with chloroform (40 ml. portions). The chloroform extract was washed with water and saturated sodium chloride solution and dried. The chloroform was evaporated in vacuo to leave a solid residue. The residue was recrystallized from ethyl acetate to yield 57 mg. of 2-amino-5(6)-formylbenzimidazole. The proton magnetic resonance spectrum indicates the correct product having a formyl group.

(E) 1-(Thiazolin-2-yl)-2-amino-5(6)-formylbenzimidazole.

Sodium hydride, 355 ml. (7.4 mmoles), as a 50 percent mineral oil suspension was washed three times with n-pentane to remove the mineral oil. The washed sodium hydride was covered with 7 ml. of dimethylformamide (DMF). A solution of 1.2 g. (7.4 mmoles) of 2-amino-5(6)-formylbenzimidazole in 20 ml. of DMF was added to the hydride suspension under anhydrous conditions. The reaction was stirred for 3 hours at room temperature to generate the anion. A solution of 895 mg. (7.4 mmole) of $\beta$-chloroethylisothiocyanate in dimethoxyethane (DME) was added to the reaction mixture and the reaction was stirred overnight. The reaction mixture was evaporated to dryness in vacuo. The residue was stirred with 140 ml. of ethyl acetate for 3 hours. The insoluble product was filtered and the filtrate was evaporated in vacuo to a residue. The residue was triturated with ethyl acetate and the mixture was centrifuged to collect more solid. The solids were combined and stirred with 50 ml. of water for several hours. The insoluble product was filtered to yield 1.1 g. of 1-(thiazolin-2-yl)-2-amino-5(6)-formylbenzimidazole.

Analysis: $C_{11}H_{10}N_4SO$ MW 242: Calcd: C, 53.64; H, 4.09; N, 22.75. Found: C, 53.86; H, 4.20; N, 22.46.

EXAMPLE 10

2-Amino-5(6)-acetylbenzimidazole (A) 4-Acetamidoacetophenone

One hundred grams of p-aminoacetophenone was added portionwise to 400 ml. of acetic anhydride. Pyridine was added to maintain a homogeneous solution. The reaction mixture was stirred for 2 hours at room temperature. The mixture was poured into 3.5 l. of cold water. The precipitated product was collected to yield 108.5 g. (93 percent) of 4-acetamidoacetophenone.

Analysis $C_{10}H_{11}NO_2$ MW 177: Calcd: C, 67.78; H, 6.26; N, 7.90. Found: C, 68.03; H, 6.47; N, 8.02.

(B) 3-Nitro-4-acetamidoacetophenone

Five grams of 4-acetamidoacetophenone were added portionwise to 25 ml. of red fuming nitric acid at 0°–5° C. After the addition was completed, the mixture was stirred for about 15 minutes. The reaction mixture was carefully poured over ice. The precipitated product was collected to yield 4.7 g. (75 percent) of 3-nitro-4-acetamidoacetophenone.

(C) 3-Nitro-4-aminoacetophenone

Sixteen grams of 3-nitro-4-acetamidoacetophenone in 160 ml. of concentrated sulfuric acid were stirred at room temperature for about one hour. The mixture was carefully poured into cold water and the precipitated product was filtered to yield 9.5 g. (73 percent) of 3-nitro-4-aminoacetophenone.

Analysis $C_8N_8N_2O_3$ MW 180: Calcd: C, 53.33; H, 4.48; N, 15.55. Found: C, 53.18; H, 4.33; N, 15.87.

(D) 2-Amino-5(6)-acetylbenzimidazole

Four and one-half grams of 3-nitro-4-aminoacetophenone were hydrogenated at 60 psi in 145 ml. of ethyl acetate with 1 g. of platinum oxide and 3 g. of Raney nickel at room temperature. Three equivalents of hydrogen were absorbed in 5 hours. The catalyst was filtered. Three grams of cyanogen bromide was added to the filtrate and the mixture was stirred for about 24 hours. The hydrobromide salt of the product precipitated and was collected to yield 2 g. of 2-amino-5(6)-acetylbenzimidazole hydrobromide.

Analysis $C_9H_9H_3O \cdot HBr$ MW 256: Calcd: C, 42.21; H, 3.94; N, 16.41. Found: C, 42.43; H, 4.09; N, 16.35.

EXAMPLES 11–12

1-(Thiazolin-2-yl)-2-amino-5(6)-acetylbenzimidazole

Five millimoles, 870 mg., of 2-amino-5(6)-acetylbenzimidazole was dissolved in a mixture of 25 ml. of dimethoxyethane (DME) and 3 ml. of dimethylformamide by warming. The solution of the ketobenzimidazole was added dropwise with stirring to 240 mg. (5 mmole) of sodium hydride as a 50 percent mineral oil suspension in DME under anhydrous conditions. The reaction was continued for about 3 hours to complete the salt formation. Six hundred milligrams (5 mmole) of β-chloroethylisothiocyanate was added dropwise and the reaction mixture was stirred overnight at room temperature. The insoluble product was filtered. The crude product was boiled in a mixture of chloroform and methanol. The insoluble product was collected, washed with water and dried. The yield of 1-(thiazolin-2-yl)-2-amino-5(6)-acetylbenzimidazole was 300 mg. (23 percent).

Analysis $C_{12}H_{12}N_4OS$ MW 260: Calcd. C, 55.37; H, 4.65; N, 21.52. Found: C, 55.15; H, 4.72; N, 21.36.

1-(thiazolin-2-yl)-2-amino-5(6)-propionylbenzimidazole was prepared from 1 g. (5.3 mmole) of 2-amino-5(6)-propionylbenzimidazole as described above to yield 100 mg. (6.9 percent) of product, recrystallized from a mixture of chloroform and methanol.

Analysis $C_{13}H_{14}N_4OS$ MW 274: Calcd: C, 56.91; H, 5.14; N, 20.42. Found: C, 56.55; H, 5.21; N, 20.12.

EXAMPLE 13

1-(Thiazolin-2-yl)-2-amino-5(6)-butyrylbenzimidazole 1-(Thiazolin-2-yl)-2-amino-5(6)-butyrylbenzimidazole was prepared from 1 g. (4.9 mmole) of 2-amino-5(6)-butyrylbenzimidazole as described in Example 11 to yield 556 mg. of product, characterized by m/e 288, 245 (m-43 or propyl group).

EXAMPLE 14

1-(Thiazolin-2-yl)-2-amino-5(6)-thenoylbenzimidazole (A) 2-Chloro-1-nitro-5-thenoylbenzene.

To a slurry of 50.4 g. (0.25 mole) of 4-chloro-3-nitrobenzoic acid in 500 ml. of benzene was added with stirring 35 g. (0.27 mole) of oxalyl chloride in 50 ml. of benzene. To the mixture was added 0.5 ml. of pyridine and the mixture was warmed and stirred until complete solution. The solvent was removed and the solid dried under vacuum. The solid was dissolved in 100 ml. of methylene chloride then added dropwise over 45 minutes to a mixture of 100 ml. of methylene chloride and 30 g. of aluminium chloride under nitrogen at 0° to 5° C. in an ice-alcohol bath. To the slurry was added 100 ml. of methylene chloride. The mixture was allowed to warm to room temperature (25° C.) for 1 hour and warmed with water until complete solution was obtained (about 45 minutes at 35°–40° C.). When the yellow precipitate began to form, the solution was cooled to 0° C., and to the solution was added dropwise at −5° to 0° C. with stirring 20 g. (0.24 mole) thiophene in 40 ml. of methylene chloride. The red solution was allowed to warm to room temperature overnight, then poured over ice. The crude product was extracted with methylene chloride. The organic layer washed with potassium hydrogen carbonate solution, dried and condensed under vacuum, dissolved in benzene, treated with carbon, filtered, and concentrated to dryness to yield 49.5 g. (74 percent) of 2-chloro-1-nitro-5-thenoylbenzene as a brown solid.

(B) 2-Nitro-4-thenoylaniline

Sixteen grams (0.06 mole) of the product of the above paragraph was amminated with 3 ml. of ammonia in 72 ml. of methanol and 13 ml. of tetramethylene sulfone at 120° C. for 15 hours. The solvent was removed under vacuum. To the residue was added 150 ml. of water, the solution was acidified with 1 ml. hydrochloric acid, filtered, washed with water, washed with diethyl ether, and dried to yield 11.5 g. (77 percent) of 2-nitro-4-thenoylaniline.

(C) 2-Amino-5(6)-thenoylbenzimidazole

Eleven grams (0.044 mole) of 2-nitro-4-thenoylaniline in 80 ml. of methanol was reduced with 1 g. of 5 percent palladium-on-carbon in 10 ml. of tetrahydrofuran at room temperature for 19 hours. The solution was filtered and 4.7 g. (0.044 mole) of cyanogen bromide was added. The mixture was stirred for 2 hours, concentrated under vacuum, diluted with 200 ml. of water, filtered, and neutralized with potassium carbonate to yield 6 g. (56 percent) of 2-amino-5(6)-thenoylbenzimidazole.

(D) 1-(Thiazolin-2-yl)-2-amino-5(6)-thenoylbenzimidazole

Five grams (0.02 mole) of 2-amino-5(6)-thenoylbenzimidazole was reacted by the procedure of Example 1 to yield 3 g. (45 percent) of 1-(thiazolin-2-yl)-2-amino-5(6)-thenoylbenzimidazole. m/e 328.

EXAMPLE 15

1-(Thiazolin-2-yl)-2-amino-5(6)-(α-hydroxyiminothienylmethyl)benzimidazole

One gram (0.003 mole) of 1-(thiazolin-2-yl)-2-amino-5(6)-thenoylbenzimidazole (prepared by the procedure of Example 14), 1.0 g. of hydroxylamine hydrochloride, and 50 ml. of methanol were heated at reflux for about 12 hours. The reaction mixture was concentrated under vacuum, redissolved in methanol, and added to 50 ml. of water with 50 ml. of buffer solution (pH=7.00). The precipitated product was collected to yield 700 mg. (68 percent) of 1-thiazolin-2-yl)-2-amino-5(6)-(α-hydroxyiminothienylmethyl)benzimidazole. m/e 343.

EXAMPLE 16

1-(Thiazolin-2-yl)-2-amino-5(6)-(α-hydroxyiminopropyl)benzimidazole

A solution of 137 mg. of 1-(thiazolin-2-yl)-2-amino-5(6)-propionylbenzimidazole (prepared by the procedure of Example 12) and 100 mg. of hydroxylamine hydrochloride, and 20 ml. of methanol was reacted according to the procedure of Example 8 to yield 55 mg. of 1-(thiazolin-2-yl)-2-amino-5(6)-(α-hydroxyiminopropyl)benzimidazole. m/e 289.

EXAMPLE 17

1-(Thiazolin-2-yl)-2-amino-5(6)-(α-acetoxyiminobenzyl)benzimidazole

Three hundred mg. (1 mole) of 1-(thiazolin-2-yl)-2-amino-5(6)-(α-hydroxyiminobenzyl)benzimidazole (prepared in Example 7) was added to 4.4 ml. of dimethylformamide with stirring. To this solution was added 54 mg. (1 mmole) of sodium methoxide. The yellow solution was stirred and 102 mg. (1 mmole) of acetic anhydride was added, and the solution stirred for 10 minutes. To the solution was added 52 ml. of water and 50 ml. of buffer solution (pH=7.00). The precipitate which formed was filtered to yield 274 mg. (88 percent) of 1-(thiazolin-2-yl)-2-amino-5(6)-(α-acetoxyiminobenzyl)benzimidazole. m/e 379.

EXAMPLE 18

A solution of 1.6 g. (0.005 mole) of 1-(thiazolin-2-yl)-2-amino-5(6)-benzoylbenzimidazole in 200 ml. of methanol, 1.1 g. (0.005 mole) of carboxymethoxylamine hemihydrochloride, and 0.3 ml. (0.003 mole) of concentrated hydrochloric acid was refluxed for 16 hours. The mixture was concentrated under vacuum to one-fourth the volume, diluted with 100 ml. of water and 200 ml. of buffer solution (pH=10.00) and stirred. A precipitate formed which was filtered, then recrystallized from ethyl acetate to obtain 0.6 g. of 1-(thiazolin-2-yl)-2-amino-5(6)-(α-methoxycarbonylmethoxyiminobenzyl)-benzimidazole.

Analysis $C_{20}H_{18}N_5O_3S$ MW 409: Calcd: C, 58.81; H, 4.44; N, 17.15. Found: C, 59.04; H, 4.39; N, 17.07.

The pH of the filtrate was then adjusted to 4 and 0.9 g. of a second precipitate isolated as above to produce 1-(thiazolin-2-yl)-2-amino-5(6)-(α-hydroxycarbonylmethoxyiminobenzyl)benzimidazole.

Analysis $C_{19}H_{16}N_5O_3S \cdot H_2O$ MW 412: Calcd: C, 55.34; H, 4.37; N, 16.99. Found: C, 55.48; H, 3.93; N, 16.54.

EXAMPLE 19

1-(Thiazolin-2-yl)-2-amino-5(6)-(1,3-dithiolan-2-yl)benzimidazole

To 1.19 g. (5 mmoles) of 2-amino-5(6)-(1,3-dithiolan-2-yl)benzimidazole in 10 ml. of dimethoxyethane was added 240 mg. (5 mmoles) of sodium hydride (50 percent in mineral oil) suspended in 5 ml. of dimethoxyethane. The orange solution was stirred at room temperature for 45 minutes, then 605 mg. (5 mmoles) of chloroethylisothiocyanate in dimethoxyethane was added and the solution stirred overnight (16 hours), filtered, and evaporated to dryness. The residue was dissolved in methanol-methylene chloride and chromatographed on a 60 g. Woelm silica gel in ethyl acetate. The desired fractions were collected, washed twice with dimethyl ether and dried to yield 78 mg. of 1-(thiazolin-2-yl)-2-amino-5(6)-(1,3-dithiolan-2-yl)benzimidazole.

EXAMPLE 20

1-(Thiazolin-2-yl)-2-amino-5(6)-α-thiocarbamylhydrazonopropyl)benzimidazole

To a solution of 274 mg. of 1-(thiazolin-2-yl)-2-amino-5(6)-propionylbenzimidazole (prepared in Example 12) was added 200 mg. of thiosemicarbazide and 1.0 ml. of 1 N hydrochloric acid in 40 ml. of methanol. The mixture was then treated according to the procedure of Example 8 to yield 169 mg. of 1-(thiazolin-2-yl)-2-amino-5(6)-(α-thiocarbamylhydrazonopropyl)benzimidazole. m/e 347.

EXAMPLE 21

1-(Thiazolin-2-yl)-2-amino-5(6)-[1(2)-methyltetrazol-5-yl]benzimidazole (A) 5-(3-Nitro-4-acetamidophenyl)tetrazole.

A solution of 10.3 g. (0.05 mole) of 3-nitro-4-acetamidobenzonitrile, 3.5 g. of sodium azide and 3.9 g. of ammonium chloride in 100 ml. of dimethylformamide was refluxed for 16 hours. The cooled reaction mixture was poured into 500 ml. of 1 N hydrochloric acid and diluted with 300 ml. of water. The yellow product precipitated and was collected to yield 10 g. (81 percent) of 5-(3-nitro-4-acetamidophenyl)tetrazole. mp. 210–213 C°. (dec).

(B) 1(2)-Methyl-5-(3-nitro-4-acetamidophenyl)tetrazole 5-(3-Nitro-4-acetamidophenyl)tetrazole, 31.7 g. (0.13 mole), was dissolved in 200 ml. of acetone. Twenty three milliliters (0.17 mole) of triethylamine was added to the reaction mixture. The mixture was stirred until it became homogeneous. Thirty milliliters of methyl iodide were added followed by the addition of another 20 ml. of methyl iodide after 12 hours at room temperature. The reaction was continued another four hours. The precipitated product was collected and the filtrate was concentrated to one fourth the original volume in vacuo. The total yield was 20 g. (59 percent) of an isomeric mixture of 1(2)-methyl-5-(3-nitro-4-acetamidophenyl)tetrazole.

Analysis $C_{10}H_{10}N_6O_3$ MW 262: Calcd: C, 45.80; H, 3.84; N, 32.05. Found: C, 45.64; H, 3.84; N, 32.18.

(C) 1(2)-Methyl-5-(3-nitro-4-aminophenyl)tetrazole

Two grams of 1(2)-methyl-5-(3-nitro-4-acetamidophenyl)tetrazole were added to 20 ml. of concentrated sulfuric acid at room temperature. The tetrazole slowly went into solution and the mixture was stirred for about 2 hours. The acid mixture was poured carefully into 200 ml. of cold water. The precipitated product was collected to yield 1.6 g. (95 percent) of 1(2)-methyl-5-(3-nitro-4-amino)tetrazole, mp. about 200° C.

Analysis $C_8H_8N_6O_2$ MW 220: Calcd: C, 43.64; H, 3.66; N, 38.17 Found: C, 43.37; H, 3.70; N, 37.89.

(D) 1(2)-Methyl-5-(3,4-diaminophenyl)tetrazole

Fourteen grams of 1(2)-methyl-5-(3-nitro-4-aminophenyl)tetrazole were hydrogenated at 60 psi with 1 g. of palladium-on-carbon in 135 ml. of ethyl acetate and 350 ml. of absolute ethanol. After 2 hours three equivalents of hydrogen were absorbed. The catalyst was filtered and the filtrate was evaporated in vacuo to yield 12 g. (98 percent) of 1(2)-methyl-5-(3,4-diaminophenyl)tetrazole.

Analysis $C_8H_{10}N_6$ MW 190: Calcd: C, 50.52; H, 5.30; N, 44.18. Found: C, 50.79; H, 5.57; N, 43.95.

(E) 1(2)-Methyl-5-(2-aminobenzimidazol-5(6)-yl)tetrazole

Cyanogen bromide, 3.2 g. (0.03 mole), was added to a slurry of 5.7 g. (0.03 mole) of 1(2)-methyl-5-(3,4-diaminophenyl)tetrazole in 300 ml. of water and 30 ml. of methanol. The mixture was stirred for 12 hours and filtered. The filtrate was neutralized with potassium carbonate. The precipitated produce was collected to yield 5.7 g. (88 percent) of 1(2)-methyl-5-(2-aminobenzimidazol-5(6)-yl)tetrazole.

Analysis $C_9H_9N_7$ MW 215: Calcd: C, 50.23; H, 4.22; N, 45.56. Found: C, 49,56; H, 4.34; N, 44.06.

(F) 1-(Thiazolin-2-yl)-2-amino-5(6)-[1(2)-methyltetrazol-5-yl]benzimidazole

When an equivalent quantity of 1(2)-methyl-5-(2-aminobenzimidazole-5(6)-yl)tetrazole was reacted according to the procedure of Example 1, there was produced 1-(thiazolin-2-yl)-2-amino-5(6)-[1(2)-methyltetrazol-5-yl]benzimidazole.

EXAMPLE 22

The following intermediates and final product were prepared by the methods of Example 21. Alkylation of the tetrazole moiety with isopropyl iodide gave only a single isomer.

(A) 1-Isopropyl-5-(3-nitro-4-aminophenyl)tetrazole, mp. 126°–128° C., yield 71 percent.

Analysis $C_{10}H_{12}N_6O_2$ MW 200: Calcd: C, 48.38; H, 4.87; N, 33.85. Found: C, 48.19; H, 4.93; N, 33.61.

(B) 1-Isopropyl-5-(3,4-diaminophenyl)tetrazole, yield 70 percent.

Analysis $C_{10}H_{14}N_6$ MW 218: Calcd: C, 55.03; H, 6.47; N, 38.50 Found: C, 55.23; H, 6.27; N, 38.73

(C) 1-Isopropyl-5-[2-aminobenzimidazol-5(6)-yl]tetrazole, mp. 232°–233° C., yield 7.3 g. (86 percent)

Analysis $C_{11}H_{13}N_7$ MW 243: Calcd: C, 54.31; H, 5.39; N, 40.30. Found: C, 54.56; H, 5.54; N, 40.53.

(D) 1-(Thiazolin-2-yl)-2-amino-5(6)-(1-isopropyltetrazol-5-yl)benzimidazole.

EXAMPLE 23

1-(Thiazolin-2-yl)-2-acetamido-5(6)-acetylbenzimidazole 1-(Thiazolin-2-yl)-2-amino-5(6)-acetylbenzimidazole, prepared by the procedure of Example 11, was reacted with acetic anhydride to provide 1-(thiazolin-2-yl)-2-acetamido-5(6)-acetylbenzimidazole.

EXAMPLE 24

1-(Thiazolin-2-yl)-2-amino-6-(α-hydroxy-α-n-butylbenzyl)benzimidazole

Four grams (12.4 mmole) of 1-(thiazolin-2-yl)-2-amino-6-benzoylbenzimidazole was added to 1,000 ml. of tetrahydrofuran under nitrogen at a temperature of −10° C. To the solution was added dropwise, under nitrogen, 50 ml. (1.6 M) of n-butyl lithium in hexane. The temperature rose to −5° C. The temperature of the solution was maintained from −5° to −10° C. for 1 hour. The solution was allowed to warm to 25° C. and maintained there for 3 hours. The solution was poured into 1 l. of water, evaporated, washed with tetrahydrofuran, and filtered to yield, as a white solid, 4.56 g. of 1-(thiazolin-2-yl)-2-amino-6-(α-hydroxy-α-n-butylbenzyl)benzimidazole, m.p. 206°–209° C.

EXAMPLE 25

1-(Thiazolin-2-yl)-2-amino-6-(α-n-butylidenebenzyl)benzimidazole

Two grams (5.26 mmole) of 1-(thiazolin-2-yl)-2-amino-6-(α-hydroxy-α-n-butylbenzyl)benzimidazole were dissolved in 250 ml. of chloroform. To the solution was added 1.3 g. of p-toluenesulfonic acid. The mixture was refluxed for 1.5 hours. The mixture was cooled to 25° C., washed twice with saturated aqueous sodium carbonate, dried, and evaporated to yield 900 mg. of 1-(thiazolin-2-yl)-2-amino-6-(α-n-butylidenebenzyl)benzimidazole, m.p. 177°–179° C.

EXAMPLE 26

1-(Thiazolin-2-yl)-2-amino-6-(α-hydroxy-α-isopropylbenzyl)benzimidazole

When the procedure of Example 24 was repeated using 5.0 g. (15.5 mmole) of 1-(thiazolin-2-yl)-2-amino-6-benzoylbenzimidazole, 500 ml. of tetrahydrofuran, and 50 ml. (2.1 M in diethyl ether) of isopropyl magnesium bromide, there was obtained 1.24 g. of 1-(thiazolin-2-yl)-2-amino-6-(α-hydroxy-α-isopropylbenzyl)benzimidazole, m.p. 212°–215° C.

EXAMPLE 27

1-(Thiazolin-2-yl)-2-amino-6-(α-isopropylidenebenzyl)benzimidazole

When the procedure of Example 25 was repeated using 1.2 g. of 1-(thiazolin-2-yl)-2-amino-6-(α-hydroxy-α-isopropylbenzyl)benzimidazole, 250 ml. of chloroform, and 1.3 g. of p-toluenesulfonic acid, there was obtained 280 mg. of 1-(thiazolin-2-yl)-2-amino-6-(α-isopropylidenebenzyl)benzimidazole, m.p. 242°–245° C. (dec.)

EXAMPLE 28

1-(Thiazolin-2-yl)-2-amino-6-(α-hydroxy-α-ethylbenzyl)benzimidazole

When the procedure of Example 24 was repeated using 2.0 g. (6.22 mmole) of 1-(thiazolin-2-yl)-2-amino-6-benzoylbenzimidazole, 23 ml. (1.25 M in benzene) of ethyl lithium, and 500 ml. of tetrahydrofuran, there was obtained 2.5 g. of 1-(thiazolin-2-yl)-2-amino-6-(α-hydroxy-α-ethylbenzyl)benzimidazole, m.p. 206°–208° C. m/e 352.

EXAMPLE 29

1-(Thiazolin-2-yl)-2-amino-6-(α-ethylidenebenzyl)benzimidazole

When the procedure of Example 25 was repeated using 1 g. of 1-(thiazolin-2-yl)-2-amino-6-(α-hydroxy-α-ethylbenzylbenzimidazole, 0.7 g. of p-toluenesulfonic acid, and 100 ml. of chloroform, there was obtained 700 mg. of crude product. The crude product was recrystallized from ethyl acetate to yield 300 mg. of 1-(thiazolin-2-yl)-2-amino-6-(α-ethylidenebenzyl)benzimidazole, m.p. 186°–187° C. then resolidifies and melts at 211° C. m/e 352.

We claim:

1. A method of suppressing the growth of a virus which comprises adding an antivirally effective amount of an active agent to a medium in which the virus is growing, said active agent being a compound of the formula

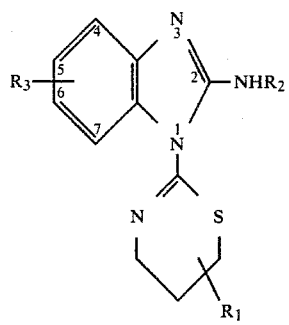

wherein
$R_1$ is hydrogen, $C_1$–$C_3$ alkyl, phenyl, or benzyl;
$R_2$ is hydrogen, or $C_1$–$C_4$ alkanoyl;
$R_3$ is at the 5 or 6 position and is 1-($C_1$–$C_3$ alkyl)tetrazol-5-yl, 1,3-dithiolan-2-yl,

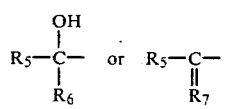

wherein $R_5$ is $C_1$–$C_3$ alkyl, $C_3$–$C_7$ cycloalkyl, ($C_3$–$C_7$ cycloalkyl)methyl, 1-($C_3$–$C_7$ cycloalkyl)ethyl, thienyl, or phenyl; $R_6$ is $C_1$–$C_7$ alkyl; $R_7$ is $C_1$–$C_7$ alkylidene; or

wherein $R_4$ is hydrogen, $C_1$–$C_7$ alkyl, $C_3$–$C_7$ cycloalkyl, ($C_3$–$C_7$ cycloalkyl)methyl, 1-($C_3$–$C_7$ cycloalkyl)ethyl, thienyl, or benzyl, phenyl or mono substituted phenyl wherein said substituents are selected from the group consisting of $C_1$–$C_4$ alkyl, $C_1$–$C_4$ alkoxy, chloro, bromo, iodo, nitro or trifluoromethyl and Z is hydroxyimino, $C_1$–$C_4$ alkoxyimino, $C_1$–$C_4$ alkanoyloxyimino, hydrazono, α-methoxycarbonylhydrazono, α-hydroxycarbonylmethoxyhydrazono, ethoxycarbonylhydrazono, carbamylhydrazono or thiocarbamylhydrazono.

2. The method of claim 1 wherein the virus is an echo virus, Mengo virus, Coxsackie virus, polio virus, rhinovirus, or influenza virus.

3. The method of claim 2 wherein the virus is an influenza virus.

4. The method of claim 2 employing as an active agent a compound wherein $R_3$ is

and Z is hydroxyimino.

5. The method of claim 4 wherein the active agent is 1-(thiazin-2-yl)-2-amino-5(6)-(hydroxyiminobenzyl)benzimidazole.

6. The method of claim 4 wherein the active agent is 1-(thiazin-2-yl)-2-amino-5(6)-(hydroxyiminomethyl)benzimidazole.

7. The method of claim 2 employing as an active agent a compound wherein $R_3$ is

and Z is $C_1$–$C_4$ alkoxyimino.

8. The method of claim 2 employing as an active agent a compound wherein $R_3$ is

and Z is $C_1$–$C_4$ alkanoyloxyimino.

9. The method of claim 2 employing as an active agent a compound wherein $R_3$ is

and Z is thiocarbamylhydrazono.

10. The method of claim 9 wherein the active agent is 1-(thiazin-2-yl)-2-amino-5(6)-(thiocarbamylhydrazonobenzyl)benzimidazole.

11. The method of claim 9 wherein the active agent is 1-(thiazin-2-yl)-2-amino-5(6)-(thiocarbamylhydrazonomethyl)benzimidazole.

12. The method of claim 2 employing as an active agent a compound where $R_3$ is

13. A method of suppressing the growth of a virus which comprises administering an antivirally effective amount of an active agent orally to a warm-blooded animal infected with a virus, said active agent being a compound of the formula

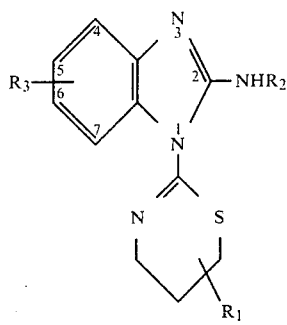

wherein
R₁ is hydrogen, $C_1$-$C_3$ alkyl, phenyl, or benzyl;
R₂ is hydrogen, or $C_1$-$C_4$ alkanoyl;
R₃ is at the 5 or 6 position and is 1-($C_1$-$C_3$ alkyl)tetrazol-5-yl, 1,3-dithiolan-2-yl,

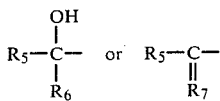

wherein R₅ is $C_1$-$C_3$ alkyl, $C_3$-$C_7$ cycloalkyl, ($C_3$-$C_7$ cycloalkyl)methyl, 1-($C_3$-$C_7$ cycloalkyl)ethyl, thienyl, or phenyl; R₆ is $C_1$-$C_7$ alkyl; R₇ is $C_1$-$C_7$ alkylidene; or

wherein R₄ is hydrogen, $C_1$-$C_7$ alkyl, $C_3$-$C_7$ cycloalkyl, ($C_3$-$C_7$ cycloalkyl)methyl, 1-($C_3$-$C_7$ cycloalkyl)ethyl, thienyl, or benzyl, phenyl or mono substituted phenyl wherein said substituents are selected from the group consisting of $C_1$-$C_4$ alkyl, $C_1$-$C_4$ alkoxy, chloro, bromo, iodo, nitro or trifluoromethyl and Z is hydroxyimino, $C_1$-$C_4$ alkoxyimino, $C_1$-$C_4$ alkanoyloxyimino, hydrazono, α-methoxycarbonylhydrazono, α-hydroxycarbonylmethoxyhydrazono, ethoxycarbonylhydrazono, carbamylhydrazono or thiocarbamylhydrazono.

14. The method of claim 13 wherein the virus is an echo virus, Mengo virus, Coxsackie virus, polio virus, rhinovirus, or influenza virus.

15. The method of claim 14 wherein the virus is an influenza virus.

16. The method of claim 14 employing as an active agent a compound wherein R₃ is

and Z is hydroxyimino.

17. The method of claim 16 wherein the active agent is 1-(thiazin-2-yl)-2-amino-5(6)-(hydroxyiminobenzyl)benzimidazole.

18. The method of claim 16 wherein the active agent is 1-(thiazin-2-yl)-2-amino-5(6)-(hydroxyiminomethyl)benzimidazole.

19. The method of claim 14 employing as an active agent a compound wherein R₃ is

and Z is $C_1$-$C_4$ alkoxyimino.

20. The method of claim 14 employing as an active agent a compound wherein R₃ is

and Z is $C_1$-$C_4$ alkanoyloxyimino.

21. The method of claim 14 employing as an active agent a compound wherein R₃ is

and Z is thiocarbamylhydrazono.

22. The method of claim 21 wherein the active agent is 1-(thiazin-2-yl)-2-amino-5(6)-(thiocarbamylhydrazonobenzyl)benzimidazole.

23. The method of claim 21 wherein the active agent is 1-(thiazin-2-yl)-2-amino-5(6)-thiocarbamylhydrazonomethyl)benzimidazole.

24. The method of claim 14 employing as an active agent a compound where R₃ is

25. A method of suppressing the growth of a virus which comprises administering an antivirally effective amount of an active agent intranasally to a warm-blooded animal infected with a virus, said active agent being a compound of the formula

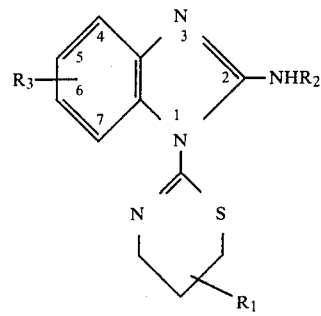

wherein
R₁ is hydrogen, $C_1$-$C_3$ alkyl, phenyl, or benzyl;
R₂ is hydrogen, or $C_1$-$C_4$ alkanoyl;
R₃ is at the 5 or 6 position and is 1-($C_1$-$C_3$ alkyl)tetrazol-5-yl, 1,3-dithiolan-2-yl,

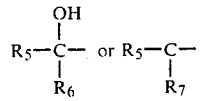

wherein R₅ is $C_1$-$C_3$ alkyl, $C_3$-$C_7$ cycloalkyl, ($C_3$-$C_7$ cycloalkyl)methyl, 1-($C_3$-$C_7$ cycloalkyl- )ethyl, thienyl, or phenyl; $R_6$ is $C_1$–$C_7$ alkyl; $R_7$ is $C_1$–$C_7$ alkylidene; or

wherein $R_4$ is hydrogen, $C_1$–$C_7$ alkyl, $C_3$–$C_7$ cycloalkyl, ($C_3$–$C_7$ cycloalkyl)methyl, 1-($C_3$–$C_7$ cycloalkyl)ethyl, thienyl, or benzyl, phenyl or mono substituted phenyl wherein said substituents are selected from the group consisting of $C_1$–$C_4$ alkyl, $C_1$–$C_4$ alkoxy, chloro, bromo, iodo, nitro or trifluoromethyl and Z is hydroxyimino, $C_1$–$C_4$ alkoxyimino, $C_1$–$C_4$ alkanoyloxyimino, hydrazono, α-methoxycarbonylhydrazono, α-hydroxycarbonylmethoxyhydrazono, ethoxycarbonylhydrazono, carbamylhydrazono or thiocarbamylhydrazono.

26. The method of claim 25 wherein the virus is an echo virus, Mengo virus, Coxsackie virus, polio virus, rhinovirus, or influenza virus.

27. The method of claim 26 wherein the virus is an influenza virus.

28. The method of claim 26 employing as an active agent a compound wherein $R_3$ is

and Z is hydroxyimino.

29. The method of claim 28 wherein the active agent is 1-(thiazin-2-yl)-2-amino-5(6)-(hydroxyiminobenzyl)-benzimidazole.

30. The method of claim 28 wherein the active agent is 1-(thiazin-2-yl)-2-amino-5(6)-(hydroxyiminomethyl)-benzimidazole.

31. The method of claim 26 employing as an active agent a compound wherein $R_3$ is

and Z is $C_1$–$C_4$ alkoxyimino.

32. The method of claim 26 employing as an active agent a compound wherein $R_3$ is

and Z is $C_1$–$C_4$ alkanoyloxyimino.

33. The method of claim 26 employing as an active agent a compound wherein $R_3$ is

and Z is thiocarbamylhydrazono.

34. The method of claim 33 wherein the active agent is 1-(thiazin-2-yl)-2-amino-5(6)-(thiocarbamylhydrazonobenzyl)benzimidazole.

35. The method of claim 33 wherein the active agent is 1-(thiazin-2-yl)-2-amino-5(6)-(thiocarbamylhydrazonomethyl)benzimidazole.

36. The method of claim 26 employing as an active agent a compound where $R_3$ is

* * * * *